United States Patent
Samartzidou et al.

(12)

(10) Patent No.: US 6,943,242 B2
(45) Date of Patent: Sep. 13, 2005

(54) DESIGN OF ARTIFICIAL GENES FOR USE AS CONTROLS IN GENE EXPRESSION ANALYSIS SYSTEMS

(75) Inventors: Hrissi Samartzidou, Sunnyvale, CA (US); Leah Turner, Sunnyvale, CA (US); Steven Daniel, The Woodlands, TX (US); Thomas Houts, Gilroy, CA (US)

(73) Assignee: Amersham Biosciences Corp., Piscataway, NJ (US)

( * ) Notice: Subject to any disclaimer, the term of this patent is extended or adjusted under 35 U.S.C. 154(b) by 343 days.

(21) Appl. No.: 10/140,545

(22) Filed: May 7, 2002

(65) Prior Publication Data

US 2003/0175726 A1 Sep. 18, 2003

Related U.S. Application Data

(60) Provisional application No. 60/289,202, filed on May 7, 2001, and provisional application No. 60/312,420, filed on Aug. 15, 2001.

(51) Int. Cl.$^7$ ........................ C07H 21/02; C07H 21/04; C12Q 1/68
(52) U.S. Cl. .................... 536/23.1; 536/24.1; 536/24.3; 536/24.31; 536/24.33; 435/6
(58) Field of Search ........................................ 536/23.1

(56) References Cited

U.S. PATENT DOCUMENTS

2002/0110828 A1   8/2002   Ferea et al.

FOREIGN PATENT DOCUMENTS

WO    WO 01/42512 A2    6/2001

OTHER PUBLICATIONS

Hockett et al (J. Immunol. Methods (1995) 187:273–285).*
Academic Press Dictionary of Science and Technology (1992) p. 1134.*
Mahmoud et al (Biochem. Biophys. Res. Comm. (1996) 228:159–164).*
Citron et al (Thrombosis Research (1997) 87(3):303–313).*
Cova et al (J. Med. Virol. (1988) 24:11–18).*
Vanderbol et al (Yeast (1994) 10:S25–S33).*
Bilban, M., et al. "Defining Signal Thresholds in DNA Microarrays: Exemplary Application for Invasive Cancer" Biomed Central Jul. 17, 2002, BMC Genomics 2002, vol. 3, No. 19 pp. 8–10.
Beibbarth, T., et al. "Processing and Quality Control of DNA Array Hybridization Data" Bioinformatics 2000, vol. 12, No. 11, pp. 1014–1022.

* cited by examiner

*Primary Examiner*—Jeffrey Fredman
(74) *Attorney, Agent, or Firm*—Yonggang Ji; Royal N. Ronning, Jr.; Stephen G. Ryan

(57) ABSTRACT

Method of producing controls for use in gene expression analysis systems such as macroarrays, real-time PCR, northern blots, SAGE and microarrays. The controls are generated either from near-random sequence of DNA, or from inter- or intragenic regions of a genome. Ten specific control sequences are also disclosed. Also presented are methods of using these controls, including as negative controls, positive controls, and as calibrators of a gene expression analysis system.

5 Claims, 20 Drawing Sheets

YIR1 nt: SEQ ID NO: 1

| | |
|---|---:|
| ttcgttggattgagtaagaaaatgtcgatactgtgttacgtttgcaaggaaa | 52 |
| agatttagttgcgattagccattcattcttgtggaaacttctttaaaaaggg | 104 |
| atggcgatggagtacttatgtccaattatgaagtcaaatttattttcaaacc | 156 |
| gttacacgtagattattttcctgcagtggtaagtatctttgaagtgttgaaa | 208 |
| gtttttggcacatatttttttgcggatgtgggcctgagtttcctgttagaa | 260 |
| acaaagatatgcttaaaactaaataacattggaaattagggcatagtcttca | 312 |
| atgttatacttaaacatcacagcaggagattgagatgattgaaagaatggtg | 364 |
| caagaaatgattcattaacattcttccaagttttgcaatatttgcaagtatt | 416 |
| actatcagactttagttgaagtgactatgctattaccaaatttcactggagc | 468 |
| cagaaaataaagatcacttagagacaaagaaaagtaacatcttcaacataa | 520 |
| gccggagctcaaaagtaggaaatcggataagaaacttgattctgttatttca | 572 |
| agtgattttttgctgtatcgcccacgttcttgttgtagatgttttgtagatg | 624 |
| tgggaccgaaagtaagtgaacagtgaagtaaacagaataggattctaaaaaa | 676 |
| gagcttataaactgttctttaaaatttttctttcgtgaatgtcctcgagct | 728 |
| atctcaaagaaaacgaaatcttcattcaacttaagtgtaggtattatttgct | 780 |
| gtttcatcaaatgcggcaccaaagtggaagtattctagtcagttagttttc | 832 |
| attgtgaggaattgatatgtcgttctctgatagaaccacgctaagttggtgt | 884 |
| tcaattttttgcaattcggtagtaattatgccttgcaacatgttttattctt | 936 |
| ttatagtgtgataccgtcaatatgatgatttgcggtggagcatgcatgtgct | 988 |
| tactagaagtgc | 1000 |

FIG. 1

YIR2 nt: SEQ ID NO: 2

| | |
|---|---|
| gcgaataaccaaaacgagactacttttaccattacaaccatttctttttc | 52 |
| cctatttctcactggttgacagaaatcagtgtgctatcatcctaccatatgc | 104 |
| gctaaacttattgtctttctcctcctagagatgctgtattccatgcatattc | 156 |
| tgaacgatgggttggtgtttttatcaagcaaggttaatcacatggcgtggct | 208 |
| tgctccacacatcagtagaaaacgcataccgcagcggaatccttaaataata | 260 |
| agtgattttactgttcatcaactacaatcggactctttcacaattacccttc | 312 |
| ttgttttccacatttactgttaaatgaagggatgtacagaaggcttaggaaa | 364 |
| acctgtgctgaatactggatggacactgcattcccacagtgaaactttata | 416 |
| gatacactgtcagttattttcgaactttcatcaagttgctgagttttagtat | 468 |
| cccttttgccttagctatatgtttgaatgagcaaaatatttgcaatgtctcta | 520 |
| gctttcttgaaatattggtttatattgagggcttggtaagatttcaaatttc | 572 |
| actttgaaatactcaggagaaaaatcatgctcttttgataatttggtgacta | 624 |
| aacatacataaaacagtttaattttgggtggtaatggctgtgtgactagcta | 676 |
| tagaaagaaaaaaattaaaaaaaaaaaaaaaatcaagtagttcctgcactg | 728 |
| cgacgtccattatagcattatgaattggtccctgatttacgcatgcgataaa | 780 |
| ctattttttagcgcagccgcatattatccgagaataacttccgacataagaaa | 832 |
| attcgcagaaaatagataaaaaactgctcttggcattcttcacttcctctat | 884 |
| tacacactgtgtcataccacaatcatctcacagtatgtatttgtatgtttat | 936 |
| acatgctataacgtaaaacaatgtagaatatatctaaatacctcacggtt | 988 |
| ttagtttagtgc | 1000 |

FIG. 2

YIR3 nt: SEQ ID NO: 3

| | |
|---|---|
| tgtttttgctatattacgtgggttttttatttatactgtatataaaagagga | 52 |
| ctgcaatagcacaagattaagatagaatggcttcaaacagccgcctttata | 104 |
| catattggtaaaagctcgcgaatcgcaccatatcccttatcctgtaatcaaa | 156 |
| tcgatctaggtgcagatacagatcaattcataaaaagaaattgaagcaccag | 208 |
| tttatcactactacactatctttttctttttttttttttttgcgaagtttc | 260 |
| gccctttgttcaatatcacttgataagttgtgggcttttctgtcactcatt | 312 |
| cggcttaaaaagtattcgttcttttgtgttttatgaaaagggaacgtgatat | 364 |
| aaaaaaacatcctttggtgtgggacatgggcttttgtttagagaatggttat | 416 |
| cactaccgcccccacccttgaaagccacagaaaatgaaaagtatgtgaata | 468 |
| aggtgtgaactctataacattttggccaaatgccacagccgatctgcatatt | 520 |
| ccaatggacataatgcaacaacaattgatgtcacattctcttacacacttcg | 572 |
| attggtccgtacgtagtactttttacataactgactcaggcgtttccttcat | 624 |
| tgaaatgctcatctattgccaagtacatagaatccacagtgcataggtttat | 676 |
| gagatgcttggaagatgtacgatcgcctgcactatattagtatatttttca | 728 |
| ggctttacaaaaccagaaagaaattaccgactgtaatacttaatttccatga | 780 |
| ttttaatcgtatggtccgtgaggaaagaggaatttaggtaaaaaaaaacct | 832 |
| ttgtctatcaaaacataaagaaaagaaaaaattaaattgaataagtcagc | 884 |
| tttttagcatgaccacagtaataatagtaatacgatatcagcatgagctgct | 936 |
| aaacattaagaattttgaattgtgttcgctgg | 969 |

FIG. 3

YIR4 nt: SEQ ID NO: 4

| | |
|---|---|
| tttcggtagtgagatggcagttcgaggggttttttattcaaaataataactt | 52 |
| ctggcttttcgcttttatatagcagaaaaaaaagccgtcgaggcgcgcgcgt | 104 |
| tcatgcaatggctcagtaacctcgggatagaaaaagggcaacaatgttgagc | 156 |
| tattttaggcacagaaactttactattcgaaagggcatccatttcatttcc | 208 |
| gattttctatctagctcactcgataatcgtaatagtacttttataaaacttt | 260 |
| agtgcgggtactgtgagagtgtgccgtaactttggtttacatttaaggtgcg | 312 |
| accagcaatgtcactactttacaacaaccgccatatggctcgagaatttca | 364 |
| ttatcacatggaatgcctgtgacaaaactgtgtaaatatctaatagaaatta | 416 |
| gatgtagctgtcacaaatatttacacaggaaagagcctgtcctacgagtatc | 468 |
| ttacatgaagattcatagaaccaatttacttgcgaatgtgaacaacctttca | 520 |
| acatcatttcataccattttccctccttatgtttggtgtcactgtaaagcg | 572 |
| gatcaaagcaaaacatagaggtacggtggtgctaagatcatgcatgacctct | 624 |
| gggtaattactacttctcccgcttgttttgagattctgtatataaatatttc | 676 |
| aaacaaaggatagagcgcggatggcaggccttatagtaaaagttattcgtt | 728 |
| ttaatcatgtgtcagtatgagattctatgacaatagtatgagaagatagggt | 780 |
| gaagtaaaagtatctgtatgactatagagtgcagttatattacaatatattg | 832 |
| aatagatcataatggtatgacgatattaaggaacatttaagttaatgacgtc | 884 |
| atggtggtatagatacgcaattgagtgtgtttatgtattattgttgaaaagt | 936 |
| agaatattttatgtttaggtgattttgatgatatttttatgtaatattgac | 988 |
| ataagtgcatataaattgagtggttagtatatggtgcaaaagtggtaca | 1037 |

FIG. 4

YIR5 nt: SEQ ID NO: 5

| | |
|---|---|
| ttagtttggaacagcagtgtagataccgtccttggatagagcgctggagata | 52 |
| gctggtctcaatctggtggagtaccatgggacaccagtgatgactctagtga | 104 |
| cttgatcagcgggaataccagtcaacatagtggtgaaatcaccgtagttgaa | 156 |
| aacagcttcagcaatttcaactgggtaagtttcagttggatgagcagcttgg | 208 |
| aacatatagtattcagccaaatgagctctgatatctgagacgtagacaccta | 260 |
| attcgaccaggttaactctttcgtcagagggagataaagtagtggtggctgg | 312 |
| ggcagcagcgacaccagcagcaatagcagcgacaccagcaacaattgaagtt | 364 |
| agtttgaccattttttcgattgaacttttgtagatcttttagtgaagatg | 416 |
| tgagctcactcgaatgtaaataacaatgccaaattgtcggaagagttaatc | 468 |
| aaagctgctctatttatatgccgttttaataagcgacggacgaacagata | 520 |
| aattgttgaatagctatttcactgctgatatttctcttacttgggctcccct | 572 |
| atcccatactcttcaccactacaaatatgcagttgccctttcttcaacaatg | 624 |
| cttttttatagatctcgtatacggatccgcgcctttgtactacctatatct | 676 |
| tattatgatatatacaggagcacaggaatgttcggtacagggatgatacctt | 728 |
| taaaggaagttttggcatgccttgacaacttcaattaatctttggccaagaa | 780 |
| aatgaaccagaaatcaatttattctgtgccctctgaacgagggcaatatc | 832 |
| caatgtttgacactaaacggttgtcaggagaaaaattgaatgtttcccaaat | 884 |
| cagaaacattaaaatccctctatatgatcagaggagtcgtacctgttagggt | 936 |
| atgagcgaggaaac | 950 |

FIG. 5

YIR6 nt: SEQ ID NO: 6

| | |
|---|---|
| aatgagttaccgtctgttacttttgggacggttttttgcactaagaacagacg | 52 |
| agtttacggttatcctcaacaagcaagcaagtatttgctaatctagatgcca | 104 |
| ttccgaatcattactcatacgttactattgagagatgttttacaatagatga | 156 |
| gaagaatacaatgtccagagctcctggtatgctagagtgcatattccaggtc | 208 |
| ttattcgaatcatatcataccgtccatttcaacaatggtgaaatgtggtcca | 260 |
| catatatcagaaatcttaacatttagtgaggagagccagtagaaaaatgtgc | 312 |
| gcaagcggaaagaagtcattcacagacacgtttaacaaaacaccaccacagc | 364 |
| agctttgtctcttgattctgatcagtttgccatcgaagaagcaaaattgtgg | 416 |
| tgttattttttcaaacaaaactttttggcaacagcagttttcttctggat | 468 |
| atttgtacttatcatccaaccgatgaaagctggtttcctgtcaacctacat | 520 |
| ttaaatggcccgtacttcttcaaaaccgctagataagcaaattaacccaact | 572 |
| tttgagcgtcctaaattccccttggctcagaagactcgttaatatgggaagt | 624 |
| ttaagtcctaccatataatcaaattggaagctttctgtgttcgaatggctat | 676 |
| tctaaccgctgggctattaatcagaggggaagtgaaatgaccgagacgtatt | 728 |
| atacgtcatgttgacatcaacaatttaaggaaaaaaataaaaaaaagcaatg | 780 |
| aaaaagggtttttttaagttgaagacccttttcaaatatatgttgctttgaa | 832 |
| ttgtatctaccgtctcgttcttctgctttaccgttttttttgccttcttt | 884 |
| agatatgtcttttatgcttgaaaggtccggctttaatgcattcatctaaacg | 936 |
| tagtattcctattttgaactgctaccaatccaccatgactttact | 982 |

FIG. 6

YIR7 nt: SEQ ID NO: 7

| | |
|---|---|
| tcctagagtagcgattcccctt cgcgtattcttacatcttcgaagagaactt | 52 |
| ctggtgtaagtataataaatattatagctctatcgaatggtgcaattattta | 104 |
| ccaaattctcaataggaatccataatactacatacgatactaatattctagt | 156 |
| attttatacttattatttcttttttattacaccagcaatcgttgcaaatta | 208 |
| tcttctgatagaatttctgagggtatcctaaacttatgccatttcttggac | 260 |
| tgtaaatcatacttggatgttgtgcattagtcaataatcggttcttgttcca | 312 |
| acgattacatgtaaatgaagggagaaataattatggtaaatcatgcggcggt | 364 |
| cctttggtgatgcagtatccatagtcactacataacaatcttagtcacctt | 416 |
| gtattgattcaccacataatcctgcagagcccgctatgtccttaatctgcgc | 468 |
| gataactctctaccctgaattttgagagcgccatagcaaaccgataaagc | 520 |
| tggcacaattaaaggtatcggtgttgtcagaattaggtgcctcctgctttt | 572 |
| ttttttcctgctcttatatccgttatatccgaatgatttttatcgcttgtt | 624 |
| taaaaaatactttcccgatatatatatatagtctccctttaaatttgtttcc | 676 |
| ggtaagttttaacaccaataaatgaaaagaaatgactacggtgatgaatat | 728 |
| gagccgcgcattgaatcaggttatgtaagtatcagaacccctaattatgatg | 780 |
| tcactcttacccttcgatggctaagcggcgactgggatgccgggaaaagctc | 832 |
| tacaaatctactaaaaagtcaaatatacagctgtaaacttctttcctcgtc | 884 |
| tacatcatggtaacgattgttcaatctttacttcgtgtctttttttttct | 936 |
| atgtactttctattccaacctatgtgaagactaaaattcaccttagtaaacg | 988 |
| taaagacaatgacgataggtgc | 1010 |

FIG. 7

YIR8 nt: SEQ ID NO: 8

```
tagttggaggttggtgagtaccagattgcttacaaaagaatagcgagccaac  52
atttgctctgcctcaggcctcttggtgctgcttgaagactcatcttatatgg  104
cttttgtatgtcatgatttgttcttgtacattatgtgttgatattaaacaaa  156
ttgatttttttttttgcgatagcaagcagataatgaaagagacaaggact  208
tggaacatccgataagactgcgccgatatcgatcttacagtccttcccttgt  260
gtcatgactttcggaaaagcatcctcgtcgactggtagtttgctgtctgtca  312
cgtgctgaagggtctgatacatttttttaaagataagagacggggtttaccc  364
ttcggaggactaagcgagatctccaagtaaagatctcgcttatcaagaaagc  416
agccaagtgtggaacgtcctttttttggtttcaaaaagatattcaacagtt  468
tacactgcagctttaattgcctcaaaaggatatcatgaggtgatctagggtc  520
agaagggaaagattacagcatcttgagttgaatcacatctgcaaaaggtggt  572
attattgacgttgctcttccttaatggaaactcatggggtttggaaggagg  624
tgcggtaatctattttttcgaacacaaaacctaaccttgaaaagaaactgt  676
ccaatttcattgaacttacctcagaacgggccggagtctttgctttcagtct  728
aacatggtctaatttcttcgaaaagcttcatttaattgttagactgtggttt  780
tacaaggaaaaaaccagtgctatactgaagcgatacccagaactaattacct  832
tgtgtgacgattcggctcagcgaaacggacatggtaaaattgggaatttgaa  884
agcaggcagcagccttgtacagcgacatgacgataggtttagaatccccatc  936
acgtacgagttgaag                                       951
```

FIG. 8

YIR11 nt: SEQ ID NO: 9

```
ccattcatatcatttagtgcttatggctacttttcattcctcaattattgta 52
aattgaccatcttaattatatttctgatattgagtaggtggacttcattagt 104
atttttacaaatattatcaccttcttatgtaggattagcattacataccctc 156
taattaaaaaaagttaacattaattacattttaaaaaaattgtaatagtat 208
gatagtaggacctgacagccatttgaataagctttcgagtgctttaacgttc 260
cactgattttatgtagttcatatgggggttagtctggtttgaggaggagaat 312
ttcagggaagcagtggccgttgaatctccctgtagggcgctgattattttta 364
tcctaataatccaaaaatgacaatgtcaataaagaaaacttaccgagttctg 416
tgaatttctccctaaaaaattactaattatacctgggcgagttttgaactct 468
ttggcaaataaacttggggtaaacctttcgattataaagacgttactgctca 520
aaaatgtgtagaagcataaggagatattctctcgtatgtttaattggagttg 572
gctttttggactctgaagtttgagtatgggaggggaagtaatcgagattag 624
attccctgatgttcacatatggggataaagaatgcttttgggatatgattg 676
tttctttccgtcgttacggttgtaggtgcaacgaattgcgtaagggtggcta 728
gccgagatttaatgacgacgcaaaagggaataactgtgacaggaagatgaat 780
tcacaaagtttataaaaagaaagggcgatgcactgctacatggttgaacaag 832
gcactacataattcacagcttgtagcttgtaaataaaaagagcattcacgcg 884
atatacgattttcaatgatcactctaagaggaacggcgaaaaatagaattca 936
atatgaactggaatgg 952
```

FIG. 9

YIR19 nt: SEQ ID NO: 10

| | |
|---|---|
| gatttaatacagtacctttcttcgctaggatctatatgcgaatatatcacat | 52 |
| atgtaaattataagctcatcgcaaaaccaaaaaaaaaaaattttcaataat | 104 |
| ttttcactaatcttcaaaaacaaatggggtaacccgtacaagagttattaaa | 156 |
| acccaaaatgacaaaatcgcgacaattcaatcctacttaattagcaataaca | 208 |
| tactagcggtagagctactatcacatgttgaaccttgatgctcaattcatt | 260 |
| gtactcaatactgctatcaaaagaaaaaaatgtattaattatattcttgtc | 312 |
| aaaatcaattttacactataagaggaaaatgttcttcagtcctagtaacatt | 364 |
| agttttctccctttgctagagactttacataatatcctagaaggtaaaattc | 416 |
| gataatacagcagtaaagtcgtatattggtagcaatccttggtgacgctgac | 468 |
| ttttttttttgtaatttattgtttagttcatgataaaaacttcaaatca | 520 |
| cttttaatctggtagacagagaaaacaaatcgaaacgaaaatagagaactac | 572 |
| gaataaaaaatataagtggagaagatcgtcactacgcattaaacaatattg | 624 |
| atcgctcaatgccagtactgcgcgtaaaagtttagtaacttaacgatttagg | 676 |
| cacaatttgagaaaaatttcgccctgcagtaagtatgttattcagtacgata | 728 |
| taaagctgaggttttatgctggcaacgttcagatttttaggttatcagcaa | 780 |
| tgttaaaatattaataggatactttattgtttgagaccaccctcaatgcc | 832 |
| agatatgttaaacgcttttttctggagtgaggtatcatagaaaaggctcga | 884 |
| gtacatcaagcacttaaaggttcaacactctactgttacttctttaagctaa | 936 |
| gctattcatacataatagtccatcaaagtgg | 967 |

FIG. 10

YIR1s nt: SEQ ID NO: 11

```
aatgtcgatactgtgttacgtttgcaaggaaaagatttagttgcgattag   50
ccattcattcttgtggaaacttctttaaaaagggatggcgatggagtact  100
tatgtccaattatgaagtcaaatttattttcaaaccgttacacgtagatt  150
attttcctgcagtggtaagtatctttgaagtgttgaaagttttttggcac  200
atattttttgcggatgtgggcctgagtttcctgttagaaacaaagatat   250
gcttaaaactaaataacattggaaattagggcatagtcttcaatgttata  300
cttaaacatcacagcaggagattgagatgattgaaagaatggtgcaagaa  350
atgattcattaacattcttccaagttttgcaatatttgcaagtattacta  400
tcagactttagttgaagtgactatgctattaccaaatttcactggagcca  450
gaaaaataaagatcacttagagacaaagaaaagtaacatcttcaacataa  500
gccggagctcaaaagtaggaaatcggataagaaacttgattctgttattt  550
caagtgatttttgctgtatcgcccacgttcttgttgtagatgttttgta   600
gatgtgggaccgaaagtaagtgacagtgaagtaaacagaataggattct   650
aaaaagagcttataaactgttctttaaattttttctttcgtgaatgtc    700
ctcgagctatctcaaagaaaacgaaatcttcattcaacttaagtgtaggt  750
attatttgctgtttcatcaaatgcggcaccaaagtggaagtattc       795
```

FIG. 11

YIR2s nt: SEQ ID NO: 12

```
tttcttttccctatttctcactggttgacagaaatcagtgtgctatcat 50
cctaccatatgcgctaaacttattgtctttctcctcctagagatgctgta 100
ttccatgcatattctgaacgatgggttggtgttttatcaagcaaggtta 150
atcacatggcgtggcttgctccacacatcagtagaaaacgcataccgcag 200
cggaatccttaaataataagtgatttactgttcatcaactacaatcgga 250
ctctttcacaattaccttcttgttttccacattactgttaaatgaagg 300
gatgtacagaaggcttaggaaaacctgtgctgaatactggatggacactg 350
cattcccacagtgaaactttatagatacactgtcagttatttcgaact 400
ttcatcaagttgctgagttttagtatccctttgcttagctatatgtttg 450
aatgagcaaaatatttgcaatgtctctagctttcttgaaatattggttta 500
tattgagggcttggtaagatttcaaatttcactttgaaatactcaggaga 550
aaaatcatgctcttttgataatttggtgactaaacatacataaacagtt 600
taattttgggtggtaatggctgtgtgactagctatagaagaaaaaaatt 650
aaaaaaaaaaaaaaatcaagtagttcctgcactgcgacgtccattata 700
gcattatgaattggtccctgatttacgcatgcgataaactattttttagcg 750
cagccgcatatt                                       762
```

FIG. 12

YIR3s nt: SEQ ID NO: 13

```
actgtatataaaagaggactgcaatagcacaagattaagatagaatggct    50
tcaaacagccgccttttatacatattggtaaaagctcgcgaatcgcacca   100
tatcccttatcctgtaatcaaatcgatctaggtgcagatacagatcaatt   150
cataaaaagaaattgaagcaccagtttatcactactacactatctttttc   200
tttttttttttttttgcgaagtttcgccctttgttcaatatcacttgat   250
aagttgtgggcttttctgtcactcattcggcttaaaagtattcgttct    300
tttgtgttttatgaaaagggaacgtgatataaaaaacatcctttggtgt   350
gggacatgggcttttgtttagagaatggttatcactaccgcccacccct   400
tgaaagccacagaaaatgaaaagtatgtgaataaggtgtgaactctata   450
acattttggccaaatgccacagccgatctgcatattccaatggacataat   500
gcaacaacaattgatgtcacattctcttacacacttcgattggtccgtac  550
gtagtacttttacataactgactcaggcgtttccttcattgaaatgctc   600
atctattgccaagtacatagaatccacagtgcataggtttatgagatgct  650
tggaagatgtacgatcgcctgcactatattagtatattttttcaggcttt  700
acaaaccagaaagaaattaccgact                            726
```

FIG. 13

YIR4s nt: SEQ ID NO: 14

```
ataataacttctggcttttcgcttttatatagcagaaaaaaaagccgtcg 50
aggcgcgcgcgttcatgcaatggctcagtaacctcgggatagaaaaggg 100
caacaatgttgagctatttaggcacagaaactttactattcgaaaaggg 150
catccatttcatttccgattttctatctagctcactcgataatcgtaata 200
gtacttttataaactttagtgcgggtactgtgagagtgtgccgtaactt 250
tggtttacatttaaggtgcgaccagcaatgtcactactttacaacaacc 300
gccatatggctcgagaatttcattatcatggaatgcctgtgacaaaac 350
tgtgtaaatatctaatagaaattagatgtagctgtcacaaatatttacac 400
aggaaagagcctgtcctacgagtatcttacatgaagattcatagaaccaa 450
tttacttgcgaatgtgaacaacctttcaacatcatttcaataccattttc 500
cctccttatgtttggtgtcactgtaaagcggatcaaagcaaaacatagag 550
gtacggtggtgctaagatcatgcatgacctctgggtaattactacttctc 600
ccgcttgttttgagattctgtatataaatatttcaaacaaaggatagag 650
cgcggatggcaggccttatagtaaagttattcgttttaatcatgtgtca 700
gtatgagattctatgacaatagtatgagaagatagggtgaagtaaaagta 750
tctgtatgactatagagtgcagttatattacaatatattgaatagatcat 800
aatggtatgacgatattaaggaacatttaagttaatgacgtcatggtgg 849
```

FIG. 14

YIR5s nt: SEQ ID NO: 15

```
agataccgtccttggatagagcgctggagatagctggtctcaatctggtg   50
gagtaccatgggacaccagtgatgactctagtgacttgatcagcgggaat  100
accagtcaacatagtggtgaaatcaccgtagttgaaaacagcttcagcaa  150
tttcaactgggtaagtttcagttggatgagcagcttggaacatatagtat  200
tcagccaaatgagctctgatatctgagacgtagacacctaattcgaccag  250
gttaactctttcgtcagagggagataaagtagtggtggctggggcagcag  300
cgacaccagcagcaatagcagcgacaccagcaacaattgaagttagtttg  350
accattttttcgattgaacttttgtagatcttttagtgaagatgtgag    400
ctcactcgaatgtaaataacaatgccaaattgtcggaaagagttaatcaa  450
agctgctctatttatatgccgttttttaataagcgacggacgaacagata  500
aattgttgaatagctatttcactgctgatatttctcttacttgggctccc  550
ctatcccatactcttcaccactacaaatatgcagttgccctttcttcaac  600
aatgcttttttatagatctcgtatacggatccgcgcctttgtactacct   650
atatcttattatgatatacaggagcacaggaatgttcggtacagggat    700
gatacctttaaa                                        712
```

FIG. 15

YIR6s nt: SEQ ID NO: 16

```
ttgggacggttttttgcactaagaacagacgagtttacggttatcctcaac 50
aagcaagcaagtatttgctaatctagatgccattccgaatcattactcat 100
acgttactattgagagatgttttacaatagatgagaagaatacaatgtcc 150
agagctcctggtatgctagagtgcatattccaggtcttattcgaatcata 200
tcataccgtccatttcaacaatggtgaaatgtggtccacatatatcagaa 250
atcttaacatttagtgaggagagccagtagaaaaatgtgcgcaagcggaa 300
agaagtcattcacagacacgtttaacaaaacaccaccacagcagctttgt 350
ctcttgattctgatcagtttgccatcgaagaagcaaaattgtggtgttat 400
ttttttcaaacaaaactttttggcaacagcagttttcttctggatattt 450
gtactttatcatccaaccgatgaaagctggtttcctgtcaacctacattt 500
aaatggcccgtacttcttcaaaaccgctagataagcaaattaacccaact 550
tttgagcgtcctaaattccccttggctcagaagactcgttaatatgggaa 600
gtttaagtcctaccatataatcaaattggaagctttctgtgttcgaatgg 650
ctattctaaccgctgggctattaatcagaggggaagtgaaatgaccgaga 700
cgtattatacgtcatgttgacatcaacaatttaaggaaaaaataaaaaa 750
aagcaatgaaaaagggttttttttaagttgaagacccttttcaaatatatg 800
ttgctttgaattgtatctaccgtctcgtttcttctgctttaccgttttttt 850
tttgccttctttagatatgtctttatgcttgaaaggtccggc         893
```

FIG. 16

YIR7s nt: SEQ ID NO: 17

```
ttcgcgtattcttacatcttcgaagagaacttctggtgtaagtataataa   50
atattatagctctatcgaatggtgcaattatttaccaaattctcaatagg  100
aatccataatactacatacgatactaatattctagtattttatacttat   150
tatttcttttttattacaccagcaatcgttgcaaattatcttctgataga  200
atttctgagggtatcctaaacttatgccatttcttggactgtaaatcat   250
acttggatgttgtgcattagtcaataatcggttcttgttccaacgattac  300
atgtaaatgaagggagaaataattatggtaaatcatgcggcggtcctttt  350
ggtgatgcagtatccatagtcactacataacaatcttagtcaccttgtat  400
tgattcaccacataatcctgcagagcccgctatgtccttaatctgcgcga  450
taactctctaccccctgaattttgagagcgccatagcaaaccgataaagc  500
tggcacaattaaaggtatcggtgttgtcagaattaggtgcctcctgcttt  550
ttttttttcctgctcttatatccgttatatccgaatgattttatcgct    600
tgtttaaaaatactttcccgatatatatatatagtctcccttttaaattt  650
gtttccggtaagttttaacaccaataaatgaaaagaaatgactacggtg   700
atgaatatgagccgcgcattgaatcaggttatgtaagtatcagaacccct  750
aattatg                                             757
```

FIG. 17

YIR8s nt: SEQ ID NO: 18

```
ccagattgcttacaaaagaatagcgagccaacatttgctctgcctcaggc   50
ctcttggtgctgcttgagactcatcttatatggcttttgtatgtcatga  100
tttgttcttgtacattatgtgttgatattaaacaaattgattttttttt  150
tttgcgatagcaagcagataatgaaagagacaaggacttggaacatcga  200
taagactgcgccgatatcgatcttacagtccttccttgtgtcatgactt  250
tcggaaaagcatcctcgtcgactggtagtttgctgtctgtcacgtgctga 300
agggtctgatacattttttaaagataagagacggggtttacccttcgga  350
ggactaagcgagatctccaagtaaagatctgcttatcaagaaagcagcc  400
aagtgtggaacgtcctttttttggtttcaaaaagatattcaacagttta  450
cactgcagctttaattgcctcaaaaggatatcatgaggtgatctagggtc 500
agaagggaaagattacagcatcttgagttgaatcacatctgcaaaaggtg 550
gtattattgacgttgctcttccttaatggaaactcatggggtttggaaag 600
gaggtgcggtaatctattttttcgaacacaaaacctaaccttgaaaaga  650
aactgtccaatttcattgaacttacctcagaacgggccggagtctttgct 700
ttcagtctaacatg                                     714
```

FIG. 18

YIR11s nt: SEQ ID NO: 19

```
ttatggctacttttcattcctcaattattgtaaattgaccatcttaatta     50
tatttctgatattgagtaggtggacttcattagtattttacaaatatta    100
tccttcttatgtaggattagcattacataccctctaattaaaaaagt     150
taacattaattcattttaaaaaaattgtaatagtatgatagtaggacc    200
tgacagccatttgaataaggtttcgagtgctttaacgttccactgatttt   250
atgtagttcatatgggggttagtctggtttgaggaggagaatttcaggga   300
agcagtggccgttaatctccctgtagggcgctgattatttttatcctaa    350
taatccaaaaatgacaatgtcaataaagaaaacttaccgagttctgtgaa   400
tttctccctaaaaaattactaattatacctgggcgagttttgaactcttt   450
ggcaaataaacttggggtaaacctttcgattataaagacgttactgctca   500
aaaatgtgtagaagcataaggagatattctctcgtatgtttaattggagt   550
tggcttttttggactctgaagtttgagtatgggagggaagtaatcgaga    600
ttagattccctgatgttcacatatggggataaagaatgcttttgggata    650
tgattgtttctttccgtcgttacggttgtaggtgcaacgaattgcgtaag   700
ggtggctagccgagatttaat                                721
```

FIG. 19

YIR19s nt: SEQ ID NO: 20

```
gctaggatctatatgcgaatatatcacatatgtaaattataagctcatcg   50
caaaaccaaaaaaaaaaaattttcaataattttcactaatcttcaaaa    100
acaaatggggtaacccgtacaagagttattaaacccaaaatgacaaaat   150
cgcgacaattcaatcctacttaattagcaataacatactagcggtagagc   200
tactatcacatgttgaaccttgaatgctcaattcattgtactcaatactg   250
ctatcaaagaaaaaaatgtattaatatattcttgtcaaaatcaattt     300
tacactataagaggaaaatgttcttcagtcctagtaacattagttttctc   350
cctttgctagagactttacataatatcctagaaggtaaaattcgataata   400
cagcagtaaagtcgtatattggtagcaatccttggtgacgctgactttt   450
ttttttgtaattttattgtttagttcatgataaaaacttcaaatcactt   500
ttaatctggtagacagagaaaacaaatcgaaacgaaaatagagaactacg   550
aataaaaaatataagtggagaagatcgtcactacgcattaaacaatatt   600
gatcgctcaatgccagtactgcgcgtaaagtttagtaacttaacgattt   650
aggcacaatttgagaaaatttcgccctgcagtaagtatgttattcagta   700
cgatataaagctgaggttttatgct                            725
```

DESIGN OF ARTIFICIAL GENES FOR USE AS CONTROLS IN GENE EXPRESSION ANALYSIS SYSTEMS

CROSS-REFERENCE TO RELATED APPLICATIONS

This application claims priority to U.S. provisional patent application Ser. No. 60/289,202, filed May 7, 2001 now abandoned; and 60/312,420, filed Aug. 15, 2001; the disclosures of which are incorporated herein by reference in their entireties.

REFERENCE TO SEQUENCE LISTING SUBMITTED ON COMPACT DISC

The present application includes a Sequence Listing filed on one CD-R disc, provided in duplicate, containing a single file named PB0120.ST25.txt, having 32 kilobytes, last modified on May 6, 2002, and recorded on May 6, 2002. The Sequence Listing contained in said file on said disc is incorporated herein by reference in its entirety.

BACKGROUND OF THE INVENTION

1. Field of the Invention

The present invention relates to a method of using artificial genes as controls in gene expression analysis systems. More particularly, the present invention relates to a method of producing Controls for use in gene expression analysis systems such as macroarrays, real-time PCR, northern blots, SAGE and microarrays, such as those provided in the Microarray ScoreCard system.

2. Description of Related Art

Gene expression profiling is an important biological approach used to better understand the molecular mechanisms that govern cellular function and growth. Microarray analysis is one of the tools that can be applied to measure the relative expression levels of individual genes under different conditions. Microarray measurements often appear to be systematically biased, however, and the factors that contribute to this bias are many and ill-defined (Bowtell, D. L., *Nature Genetics* 21, 25–32 (1999); Brown, P. P. and Botstein, D., *Nature Genetics* 21, 33–37 (1999)). Others have recommended the use of "spikes" of purified mRNA at known concentrations as controls in microarray experiments. Affymetrix includes several for use with their GeneChip products. In the current state of the art, these selected genes are actual genes selected from very distantly related organisms. For example, the human chip (designed for use with human mRNA) includes control genes from bacterial and plant sources. Affymetrix sells mRNA corresponding to these genes for spiking into the labeling reaction and inclusion in the hybridization reaction.

Each of the prior art controls includes transcribed sequences of DNA from some source. As a result, that source cannot be the subject of a hybridization experiment using those controls due to the inherent hybridization of the controls to its source. What is needed, therefore, is a set of controls which do not hybridize with the DNA of any source which may be the subject of an experiment. More desirably, there is a need for a control for gene expression analysis which does not hybridize with any known source.

SUMMARY OF THE INVENTION

Accordingly, this invention provides a process of producing controls that are useful in gene expression analysis systems designed for any species and which can be tested to insure lack of hybridization with mRNA from sources other than the control DNA itself.

The invention relates in a first embodiment to a process for producing at least one control for use in a gene expression analysis system. The process comprises selecting at least one non-transcribed (inter- or intragenic) region of genomic DNA from a known sequence, designing primer pairs for said at least one non-transcribed region and amplifying said at least one non-transcribed region of genomic DNA to generate corresponding double stranded DNA, then cloning said double stranded DNA using a vector to obtain additional double stranded DNA and formulating at least one control comprising said double stranded DNA.

The present invention relates in a second embodiment to a process of producing at least one control for use in a gene expression analysis system wherein testing of said at least one non-transcribed region to ensure lack of hybridization with mRNA from sources other than said at least one non-transcribed region of genomic DNA is performed.

The present invention in a third embodiment relates to said process further comprising purifying said DNA and mRNA, determining the concentrations thereof and formulating at least one control comprising said DNA or of said mRNA at selected concentrations and ratios.

Another embodiment of the present invention is a control for use in a gene expression analysis system comprising a known amount of at least one DNA generated from at least one non-transcribed region of genomic DNA from a known sequence, or comprising a known amount of at least one mRNA generated from DNA generated from at least one non-transcribed region of genomic DNA from a known sequence. The present invention may optionally include generating mRNA complementary to said DNA and formulating at least one control comprising said mRNA, by optionally purifying said DNA and mRNA, determining the concentrations thereof and formulating at least one control comprising said DNA or of said mRNA at selected concentrations and ratios.

Another embodiment of the present invention is a control for use in a gene expression analysis system wherein a known amount of at least one DNA sequence generated from at least one non-transcribed region of genomic DNA from a known sequence, a known amount of at least one mRNA generated from DNA generated from at least one non-transcribed region of genomic DNA from a known sequence is included, and the aforementioned control wherein, said DNA and mRNA do not hybridize with any DNA or mRNA from a source other than the at least one non-transcribed region of genomic DNA.

The present invention, relates to a method of using said control, as a negative control in a gene expression analysis system by adding a known amount of said control containing a known amount of DNA, to a gene expression analysis system as a control sample and subjecting the sample to hybridization conditions in the absence of complementary labeled mRNA and examining the control sample for the absence or presence of signal.

Further, said controls can be used in a gene expression analysis system by adding a known amount of a said control containing a known amount of DNA to a gene expression analysis system as a control sample and subjecting the sample to hybridization conditions, in the presence of a said control containing a known amount of labeled complementary mRNA, and measuring the signal values for the labeled mRNA and determining the expression level of the DNA based on the signal value of the labeled mRNA.

Additionally, said controls may be used as calibrators in a gene expression analysis system by adding a known amount of a said control containing known amounts of several DNA sequences to a gene expression analysis system as control samples and subjecting the samples to hybridization conditions in the presence of a said control containing known amounts of corresponding complementary labeled mRNAs, each mRNA being at a different concentration and measuring the signal values for the labeled mRNAs and constructing a dose-response or calibration curve based on the relationship between signal value and concentration of each mRNA.

Also, the present invention relates to a method of using said controls as calibrators for gene expression ratios in a two-color gene expression analysis system by adding a known amount of at least one of said controls containing a known amount of DNA to a two-color gene expression analysis system as control samples and subjecting the samples to hybridization conditions in the presence of a said control containing known amounts of two differently labeled corresponding complementary labeled mRNAs for each DNA sample present and measuring the ratio of the signal values for the two differently labeled mRNAs and comparing the signal ratio to the ratio of concentrations of the two or more differently labelled mRNAs.

A further embodiment of the present invention is a process of producing controls that are useful in gene expression analysis systems designed for any species and which can be tested to insure lack of hybridization with mRNA from sources other than the synthetic sequences of DNA from which the control is produced.

One or more such controls can be produces by a process comprising synthesizing a near-random sequence of non-transcribed DNA, designing primer pairs for said at least one near random sequence and amplifying said non-transcribed DNA to generate corresponding double stranded DNA, then cloning said double stranded DNA using a vector to obtain additional double stranded DNA and formulating at least one control comprising said double stranded DNA.

The process can also be used to produce at least one control for use in a gene expression analysis system wherein testing of said sequence of non-transcribed synthetic DNA to ensure lack of hybridization with mRNA from sources other than said sequence of non-transcribed DNA is performed.

Additionally, mRNA complementary to said synthetic DNA can be generated and formulated to generate at least one control comprising said mRNA.

DNA and mRNA can be subsequently purified, the concentrations thereof determined, and one or more controls comprising said DNA or said mRNA at selected concentrations and ratios be formulated.

Another embodiment of the present invention is a control for use in a gene expression analysis system produced by the process comprises synthesizing a near-random sequence of DNA, designing primer pairs for said synthetic DNA and amplifying said DNA to generate corresponding double stranded DNA, then cloning said double stranded DNA using a vector to obtain additional double stranded DNA and formulating at least one control comprising a known amount of at least one said double stranded DNA or a known amount of at least one mRNA generated from said DNA, and optionally, wherein, said DNA and mRNA do not hybridize with any DNA or mRNA from a source other than said DNA sequence of non-transcribed DNA.

The present invention, additionally, relates to a method of using said controls containing a known amount of DNA, as a negative control in a gene expression analysis system including adding a known amount of said control containing a known amount of DNA to a gene expression analysis system as a control sample, and subjecting the sample to hybridization conditions in the absence of complementary labeled mRNA and examining the control sample for the absence or presence of signal.

Further, said controls may be used in a gene expression analysis system wherein a known amount of a said control containing a known amount of DNA is added to a gene expression analysis system as a control sample and subjecting the sample to hybridization conditions in the presence of a said control containing a known amount of labeled complementary mRNA and measuring the signal values for the labeled mRNA and determining the expression level of the DNA based on the signal value of the labeled mRNA.

The present invention, also relates to a method of using said controls as calibrators in a gene expression analysis system including adding known amounts of a said control containing known amounts of several DNAs to a gene expression analysis system as control samples and subjecting the samples to hybridization conditions in the presence of a said control containing known amounts of corresponding complementary labeled mRNAs, each mRNA being at a different concentration and measuring the signal values for the labeled mRNAs and constructing a dose-response or calibration curve based on the relationship between signal value and concentration of each mRNA.

The present invention, additionally, relates to a method of using said controls as calibrators for gene expression ratios in a two-color gene expression analysis system comprising adding a known amount of at least one of said controls containing a known amount of DNA to a two-color gene expression analysis system as control samples and subjecting the samples to hybridization conditions in the presence of a said control containing known amounts of two differently labeled corresponding complementary labeled mRNAs for each DNA sample present and measuring the ratio of the signal values for the two differently labeled mRNAs and comparing the signal ratio to the ratio of concentrations of the two or more differently labeled mRNAs.

Further embodiments and uses of the current invention will become apparent from a consideration of the ensuing description.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which:

FIG. 1 presents the control nucleotide sequences of YIR1;

FIG. 2 presents the control nucleotide sequences of YIR2;

FIG. 3 presents the control nucleotide sequences of YIR3;

FIG. 4 presents the control nucleotide sequences of YIR4;

FIG. 5 presents the control nucleotide sequences of YIR5;

FIG. 6 presents the control nucleotide sequences of YIR6;

FIG. 7 presents the control nucleotide sequences of YIR7;

FIG. 8 presents the control nucleotide sequences of YIR8;

FIG. 9 presents the control nucleotide sequences of YIR11;

FIG. 10 presents the control nucleotide sequences of YIR19;

FIG. 11 presents the nucleotide sequences of YIR1s used in a spike mix;

FIG. 12 presents the nucleotide sequences of YIR2s used in a spike mix;

FIG. 13 presents the nucleotide sequences of YIR3s used in a spike mix;

FIG. 14 presents the nucleotide sequences of YIR4s used in a spike mix;

FIG. 15 presents the nucleotide sequences of YIR5s used in a spike mix;

FIG. 16 presents the nucleotide sequences of YIR6s used in a spike mix;

FIG. 17 presents the nucleotide sequences of YIR7s used in a spike mix;

FIG. 18 presents the nucleotide sequences of YIR8s used in a spike mix;

FIG. 19 presents the nucleotide sequences of YIR11s used in a spike mix; and

FIG. 20 presents the nucleotide sequences of YIR19s used in a spike mix.

DETAILED DESCRIPTION OF THE INVENTION

The present invention teaches Controls for use in gene expression analysis systems such as microarrays. Many have expressed interest in being able to obtain suitable genes and spikes as controls for inclusion in their arrays.

An advantage of the Controls of this invention is that a single set can be used with assay systems designed for any species, as these Controls will not be present unless intentionally added. This contrasts with the concept of using genes from "distantly related species." For example, an analysis system directed at detecting human gene expression might employ a *Bacillus subtilis* gene as control, which may not be present in a human genetic material. But this control might be present in bacterial genetic material (or at least, cross hybridize), thus it may not be a good control for an experiment on bacterial gene expression. The novel Controls presented here provide an advantage over the state of the art in that the same set of controls can be used without regard to the species for the test sample RNA.

The present invention employs the novel approaches of using either non-transcribed genomic sequences or totally random synthetic sequences as a template and generating both DNA and complementary "mRNA" from such sequences, for use as controls. The Controls could be devised de novo by designing near-random sequences and synthesizing them resulting in synthetic macromolecules as universal controls. Totally synthetic random DNA fragments are so designed that they do not cross-hybridize with each other or with RNA from any biologically relevant species (meaning species whose DNA or RNA might be present in the gene expression analysis system). The cost of generating such large synthetic DNA molecules can be high. However, they only need to be generated a single time. Additionally, fragment size can be increased by ligating smaller synthetic fragments together by known methods. In this way, fragments large enough to be easily cloned can be created. Through cloning and PCR sufficient quantities of DNA for use as controls can be produced and mRNA can be generated by in vitro transcription for use in controls.

A simpler approach is to identify sequences from the non-transcribed regions of genomic DNA from an organism, and use these as a template for synthesis via PCR (polymerase chain reaction). Ideally, sequences of around 1000 bases (could range from 500 to 2000 bases) are selected based on computer searches of publicly accessible sequence data. The criteria for selection include:

1. The sequence must be from a non-transcribed region (intergenic or intronic region); and
2. The sequence must not have homology with or be predicted to hybridise with any known/published gene or expressed sequence tag (EST).

PCR primer pairs are designed for the selected sequence (s) and PCR is performed using genomic DNA (as a template) to generate PCR fragments (dsDNA) corresponding to the non-transcribed sequence(s) as the control DNA. Additional control DNA can be cloned using a vector and standard techniques. Subsequently, standard techniques such as in vitro transcription are used to generate mRNA (complementary to the cDNA and containing a poly-A tail) as the control mRNA. Standard techniques are used for purifying the Control DNA and Control mRNA products, and for estimating their concentrations.

Empirical testing is also performed to ensure lack of hybridization between the Control DNA on the array and other mRNAs, as well as with mRNA from important gene expression systems (e.g., human, mouse, *Arabidopsis*, etc.).

The above approaches were used to generate ten control sequences from intergenic regions of the yeast *Saccharomyces cerevisiae* genome. Specifically, using yeast genome sequence data publicly available at The *Saccharomyces* Genome Database web page maintained by the Department of Genetics at the School of Medicine, Stanford University, intergenic regions approximately 1 kb in size were identified. These sequences were BLAST'd and those showing no homology to other sequences were identified as candidates for artificial gene controls. Candidates were analyzed for GC-content and a subset with a GC-content of ≧36% were identified. Specific primer sequences have been identified and synthesized. PCR products amplified with the specific primers have been cloned directly into the pGEM™-T Easy vector (Promega Corp., Madison, Wis.). Both array targets and templates for spike mRNA have been amplified from these clones using distinct and specific primers.

To maximize the chances of identifying 10 control sequences, a greater number of intergenic regions have been cloned for testing. All candidate sequences were spotted on glass microarray slides and hybridized with each candidate spike mRNA independently to identify those that cross-hybridize. Ten candidates exhibiting specific hybridization were chosen to form the specific set of controls. When used as controls, all of the ten yeast intergenic regions (YIRs) were generated by PCR with specific primers (Table 1), using 5 ng of cloned template (plasmid DNA) and a primer concentration of 0.5 µM in a 100 µl reaction volume, and cycled as follows: 35 cycles of

TABLE 1

Primers used for amplification of controls.

| Target | Forward Primer | | Reverse Primer | |
|---|---|---|---|---|
| YIR1 | TTCGTTGGATTGAGTAAGAA | SEQ ID NO: 21 | GCACTTCTAGTAAGCACATG | SEQ ID NO: 31 |
| YIR2 | GCGAATAACCAAAACGAGAC | SEQ ID NO: 22 | GCACTAAACTAAAACCGTGA | SEQ ID NO: 32 |

TABLE 1-continued

Primers used for amplification of controls.

| Target | Forward Primer | | Reverse Primer | |
|---|---|---|---|---|
| YIR3 | TGTTTTTGCTATATTACGTGGG | SEQ ID NO: 23 | CCAGCGAACACAATTCAAAA | SEQ ID NO: 33 |
| YIR4 | TTTCGGTAGTGAGATGGCAG | SEQ ID NO: 24 | TGTACCACTTTTGCACCATA | SEQ ID NO: 34 |
| YIR5 | TTAGTTTGGAACAGCAGTGT | SEQ ID NO: 25 | GTTTCCTCGCTCATACCCTA | SEQ ID NO: 35 |
| YIR6 | AATGAGTTACCGTCTGTTAC | SEQ ID NO: 26 | AGTAAAGTCATGGTGGATTG | SEQ ID NO: 36 |
| YIR7 | TCCTAGAGTAGCGATTCCCC | SEQ ID NO: 27 | GCACCTATCGTCATTGTCTT | SEQ ID NO: 37 |
| YIR8 | TAGTTGGAGGTTGGTGAGTA | SEQ ID NO: 28 | CTTCAACTCGTACGTGATGG | SEQ ID NO: 38 |
| YIR11 | CCATTCATATCATTTAGTGC | SEQ ID NO: 29 | CCATTCCAGTTCATATTGAA | SEQ ID NO: 39 |
| YIR19 | GATTTAATACAGTACCTTTCTTCGC | SEQ ID NO: 30 | CCACTTTGATGGACTATTATGTATG | SEQ ID NO: 40 |

94° C. 20 sec., 52° C. 20 sec., 72° C. 2 min., followed by extension at 72° C. for 5 min.

All YIR control mRNAs for the spike mix are generated by in vitro transcription. Templates for in vitro transcription (IVT) are generated by amplification with specific primers that are designed to introduce a T7 RNA polymerase promoter on the 5' end and a polyT (T21) tail on the 3' end of the PCR products (see Table 2). Run-off mRNA is produced using 1 µl of these PCR products per reaction with the AmpliScribe system (Epicentre, Madison, Wis.). IVT products are purified using the RNAEasy system (Qiagen Inc., Valencia, Calif.) and quantified by spectrophotometry.

FIG. 1 through FIG. 10 presents the nucleotide sequences of the ten YIR controls, while FIGS. 11 through 20 presents the nucleotide sequences of the ten YIRs ('s' for spike mix) as used in a spike mix. The primer sequences used for amplifying the controls were listed in Table 1, the primer sequences used for amplifying spike mix templates were listed in Table 2. These sequences are further presented in the Sequence Listing, incorporated herein by reference in its entirety, as follows:

| | |
|---|---|
| SEQ ID NO: 1–8 | nt, control nucleotide sequences YIR1 through YIR8; |
| SEQ ID NO: 9 | nt, control nucleotide sequences YIR11; |
| SEQ ID NO: 10 | nt, control nucleotide sequences YIR19; |

TABLE 2

Primers used for amplification of in vitro transcription targets.

| Template | Forward Primer | | Reverse Primer | |
|---|---|---|---|---|
| YIR1 | GCATTAGCGGCCGCGAAATTAATACGACTCACTATAGGGAGAAATGTCGATACTGTGTTACG | SEQ ID NO: 41 | TTTTTTTTTTTTTTTTTTTTTGAATACTTCCACTTTGGTGC | SEQ ID NO: 51 |
| YIR2 | GCATTAGCGGCCGCGAAATTAATACGACTCACTATAGGGAGATTTCTTTTTCCCTATTTCTCACTGG | SEQ ID NO: 42 | TTTTTTTTTTTTTTTTTTTTTAATATGCGGCTGCGCTAAAA | SEQ ID NO: 52 |
| YIR3 | GCATTAGCGGCCGCGPAATTAATACGACTCACTATAGGGAGAACTGTATATAAAAGAGGACTGC | SEQ ID NO: 43 | TTTTTTTTTTTTTTTTTTTTTAGTCGGTAATTTCTTTCTGG | SEQ ID NO: 53 |
| YIR4 | GCATTAGCGGCCGCGAAATTAATACGACTCACTATAGGGAGAATAATAACTTCTGGCTTTTCGC | SEQ ID NO: 44 | TTTTTTTTTTTTTTTTTTTTTCCACCATGACGTCATTAACTTAAAT | SEQ ID NO: 54 |
| YIR5 | GCATTAGCGGCCGCGAAATTAATACGACTCACTATAGGGAGAAGATACCGTCCTTGGATAGA | SEQ ID NO: 45 | TTTTTTTTTTTTTTTTTTTTTTTAAAGGTATCATCCCTGT | SEQ ID NO: 55 |
| YIR6 | GCATTAGCGGCCGCGAAATTAATACGACTCACTATAGGGAGATTGGGACGGTTTTTGCACTAAGAA | SEQ ID NO: 46 | TTTTTTTTTTTTTTTTTTTTTGCCGGACCTTTCAAGCATAA | SEQ ID NO: 56 |

TABLE 2-continued

Primers used for amplification of in vitro transcription targets.

| Template | Forward Primer | | Reverse Primer | |
|---|---|---|---|---|
| YIR7 | GCATTAGCGGCCGCGAAATTAATA CGACTCACTATAGGGAGATTCGCG TATTCTTACATCTT | SEQ ID NO: 47 | TTTTTTTTTTTTTTTTTTTTCAT AATTAGGGGTTCTGATA | SEQ ID NO: 57 |
| YIR8 | GCATTAGCGGCCGCGAAATTAATA CGACTCACTATAGGGAGACCAGAT TGCTTACAAAAGAA | SEQ ID NO: 48 | TTTTTTTTTTTTTTTTTTTTCAT GTTAGACTGAAAGCAAA | SEQ ID NO: 58 |
| YIR11 | GCATTAGCGGCCGCGAAATTAATA CGACTCACTATAGGGAGATTATGG CTACTTTTCATTCC | SEQ ID NO: 49 | TTTTTTTTTTTTTTTTTTTTATT AAATCTCGGCTAGCCAC | SEQ ID NO: 59 |
| YIR19 | GCATTAGCGGCCGCGAAATTAATA CGACTCACTATAGGGAGAGCTAGG ATCTATATGCGAAT | SEQ ID NO: 50 | TTTTTTTTTTTTTTTTTTTTAGC ATAAAACCTCAGCTTTA | SEQ ID NO: 60 |

| | |
|---|---|
| SEQ ID NO: 11–18 | nt, spike mix nucleotide sequences YIR1s through YIR8s; |
| SEQ ID NO: 19 | nt, spike mix nucleotide sequence YIR11s; |
| SEQ ID NO: 20 | nt, spike mix nucleotide sequence YIR19s; |
| SEQ ID NO: 21–28 | nt, forward primer sequences for amplification of controls YIR1 through YIR8; |
| SEQ ID NO: 29 | nt, forward primer sequence for amplification of control YIR11; |
| SEQ ID NO: 30 | nt, forward primer sequence for amplification of control YIR19; |
| SEQ ID NO: 31–38 | nt, reverse primer sequences for amplification of controls YIR1 through YIR8; |
| SEQ ID NO: 39 | nt, reverse primer sequence for amplification of controls YIR11; |
| SEQ ID NO: 40 | nt, reverse primer sequence for amplification of controls YIR19; |
| SEQ ID NO: 41–48 | nt, forward primer sequences for amplification of in vitro transcription templates YIR1s through YIR8s; |
| SEQ ID NO: 49 | nt, forward primer sequence for amplification of in vitro transcription templates YIR11s; |
| SEQ ID NO: 50 | nt, forward primer sequence for amplification of in vitro transcription templates YIR19s; |
| SEQ ID NO: 51–58 | nt, reverse primer sequences for amplification of in vitro transcription templates YIR1s through YIR8s; |
| SEQ ID NO: 59 | nt, reverse primer sequence for amplification of in vitro transcription templates YIR11s; |
| SEQ ID NO: 60 | nt, reverse primer sequence for amplification of in vitro transcription templates YIR19s; |

The following examples demostrate how these Control DNA and Control mRNA are then used as controls in microarray gene expression experiments:

1. Control DNA included in the array, but for which no complementary artificial mRNA is spiked into the RNA sample, serves as a negative control;
2. Several different Control DNA samples may be included in an array, and the complementary Control mRNA for each is included at a known concentration, each having a different concentration of mRNA. The signals from the array features corresponding to these Controls or Calibrators may be used to construct a "dose-response curve" or calibration curve to estimate the relationship between signal and amount of mRNA from the sample;
3. In two-color microarray gene expression studies, it is possible to include different, known, levels of Control mRNA complementary to Control DNA in the labeling reaction for each channel. Comparing the ratio of signals for the two dyes from that gene can be compared to the ratio of concentrations of the two Control mRNA molecules. This can serve as a test of the accuracy of the system for determining gene expression ratios.
4. Mixtures of several different Control mRNA species can be prepared (spike mixes) at known concentrations and ratios to simplify the experimental protocol while providing a comprehensive set of precision and accuracy information. Table 3 demonstrates one embodiment of this concept. The presence of the dynamic range controls (those included in the labeling reaction at a ratio of 1:1) allows the user to determine the sensitivity of the system. They are also useful for demonstrating the precision of the normalisation method used. For the ratio controls, individual mRNAs are spiked into the two labeling reactions at different concentrations, such that a specific sequence is represented at different levels in each color.

The above examples illustrate specific aspects of the present invention and are not intended to limit the scope thereof in any respect and should not be so construed.

Those skilled in the art having the benefit of the teachings of the present invention as set forth above, can effect numerous modifications thereto. These modifications are to be construed as being encompassed within the scope of the present invention as set forth in the appended claims.

TABLE 3

Suggested Control mNRA spike mix composition for two-color gene expression ratio experiments.

| Control | Target Cy3:Cy5 Ratio | Conc. In mix (pg/5µl mix) Cy3 | Conc. In mix (pg/5µl mix) Cy5 | Relative abundance* |
|---|---|---|---|---|
| YIR1s | 1:1 | 33 000 | 33 000 | 3.3% |
| YIR2s | 1:1 | 10 000 | 10 000 | 1% |
| YIR3s | 1:1 | 1 000 | 1 000 | 0.1% |
| YTR4s | 1:1 | 330 | 330 | 0.033% |
| YIR5s | 1:1 | 100 | 100 | 0.01% |
| YIR6s | 1:1 | 33 | 33 | 0.0033% |
| YIR7s | 1:3 | 1 000 | 3 000 | NA |
| YTR8s | 3:1 | 3 000 | 1 000 | NA |
| YTR11s | 1:10 | 1 000 | 10 000 | NA |
| YIR19s | 10:1 | 10 000 | 1 000 | NA |

*For the labeling reactions, add 5 µl of the appropriate spike mix per microgram of Control mRNA. Use the spiked Control mRNA in the first-strand cDNA synthesis reaction. The spiked Control mRNA can be labeled using oligo dT and/or random primers.

What is claimed is:

1. A control for use in a gene expression analysis system comprising:

a known amount of at least one DNA target generated from at least one intergenic or intronic region of genomic DNA from a known sequence; or a known amount of at least one spike mRNA generated from DNA generated from said at least one intergenic or intronic region of genomic DNA from a known sequence, wherein (a) said at least one DNA is selected from the group consisting of
  (i) SEQ ID No: 1; and
  (ii) a complete complement of the sequence set forth in (i); or (b) said at least one mRNA is transcribed from the group consisting of
  (i) SEQ ID No: 11; and
  (ii) a complete complement of the sequence set forth in (i).

2. The control of claim 1 wherein, said at least one DNA target or spike mRNA do not hybridize at high stringency with any DNA or mRNA from a source other than said at least one intergenic or intronic region of genomic DNA.

3. The control of claim 1, wherein said at least one DNA target or spike mRNA is formulated at selected concentrations and ratios.

4. The control of claim 1, wherein said at least one DNA target is addressably disposed upon a substrate.

5. The control of claim 1, wherein said at least one spike mRNA is detectably labeled.

* * * * *

SEQUENCE LISTING

<160> NUMBER OF SEQ ID NOS: 60

<210> SEQ ID NO 1
<211> LENGTH: 1000
<212> TYPE: DNA
<213> ORGANISM: Saccharomyces cerevisiae

<400> SEQUENCE: 1

```
ttcgttggat tgagtaagaa aatgtcgata ctgtgttacg tttgcaagga aaagatttag      60
ttgcgattag ccattcattc ttgtggaaac ttctttaaaa agggatggcg atggagtact     120
tatgtccaat tatgaagtca aatttatttt caaaccgtta cacgtagatt attttcctgc     180
agtggtaagt atctttgaag tgttgaaagt ttttggcac atattttttt gcggatgtgg     240
gcctgagttt cctgttagaa acaaagatat gcttaaaact aaataacatt ggaaattagg     300
gcatagtctt caatgttata cttaaacatc acagcaggag attgagatga ttgaaagaat     360
ggtgcaagaa atgattcatt aacattcttc caagttttgc aatatttgca agtattacta     420
tcagacttta gttgaagtga ctatgctatt accaaatttc actggagcca gaaaaataaa     480
gatcacttag agacaaagaa aagtaacatc ttcaacataa gccggagctc aaaagtagga     540
aatcggataa gaaacttgat tctgttattt caagtgattt tttgctgtat cgcccacgtt     600
cttgttgtag atgttttgta gatgtgggac cgaaagtaag tgaacagtga agtaaacaga     660
ataggattct aaaaaagagc ttataaactg ttctttaaaa ttttttcttt cgtgaatgtc     720
ctcgagctat ctcaaagaaa acgaaatctt cattcaactt aagtgtaggt attatttgct     780
gtttcatcaa atgcggcacc aaagtggaag tattctagtc agttagtttt tcattgtgag     840
gaattgatat gtcgttctct gatagaacca cgctaagttc gtgttcaatt ttttgcaatt     900
cggtagtaat tatgccttgc aacatgtttt attctttat agtgtgatac cgtcaatatg     960
atgatttgcg gtggagcatg catgtgctta ctagaagtgc                          1000
```

<210> SEQ ID NO 2
<211> LENGTH: 1000
<212> TYPE: DNA
<213> ORGANISM: Saccharomyces cerevisiae

<400> SEQUENCE: 2

```
gcgaataacc aaaacgagac tactttttac cattacaacc attttctttt tccctatttc      60
tcactggttg acagaaatca gtgtgctatc atcctaccat atgcgctaaa cttattgtct     120
ttctcctcct agagatgctg tattccatgc atattctgaa cgatggttg gtgttttat       180
caagcaaggt taatcacatg gcgtggcttg ctccacacat cagtagaaaa cgcataccgc     240
agcggaatcc ttaaataata agtgatttta ctgttcatca actacaatcg gactctttca     300
caattcccct tcttgttttc cacatttact gttaaatgaa gggatgtaca gaaggcttag     360
gaaaacctgt gctgaatact ggatggacac tgcattccca cagtgaaact tttatagata     420
cactgtcagt tattttcgaa ctttcatcaa gttgctgagt tttagtatcc ctttgcctta     480
gctatatgtt tgaatgagca aaatatttgc aatgtctcta gctttcttga atatattggtt   540
tatattgagg gcttggtaag atttcaaatt tcactttgaa atactcagga gaaaaatcat    600
gctcttttga taatttggtg actaaacata cataaaacag tttaattttg ggtggtaatg    660
gctgtgtgac tagctataga aagaaaaaaa ttaaaaaaaa aaaaaaaaat caagtagttc    720
ctgcactgcg acgtccatta tagcattatg aattggtccc tgatttacgc atgcgataaa    780
ctattttttag cgcagccgca tattatccga gaataacttc cgacataaga aaattcgcag   840
aaaatagata aaaaactgct cttggcattc ttcacttcct ctattacaca ctgtgtcata    900
ccacaatcat ctcacagtat gtatttgtat gtttatacat gctataacgt aaaacaatgt    960
agaatatata tctaaatacc tcacggtttt agtttagtgc                         1000
```

<210> SEQ ID NO 3
<211> LENGTH: 969
<212> TYPE: DNA
<213> ORGANISM: Saccharomyces cerevisiae

<400> SEQUENCE: 3

```
tgttttttgct atattacgtg ggttttttat ttatactgta tataaaagag gactgcaata    60
gcacaagatt aagatagaat ggcttcaaac agccgccttt tatacatatt ggtaaaagct    120
cgcgaatcgc accatatccc ttatcctgta atcaaatcga tctaggtgca gatacagatc    180
aattcataaa aagaaattga agcaccagtt tatcactact acactatctt ttctttttt     240
ttttttttt gcgaagtttc gccctttgtt caatatcact tgataagttg tgggcttttt     300
ctgtcactca ttcggcttaa aaagtattcg ttcttttgtg ttttatgaaa agggaacgtg    360
atataaaaa acatcctttg gtgtgggaca tgggcttttg tttagagaat ggttatcact     420
accgccccca cccttgaaag ccacagaaaa tgaaaaagta tgtgaataag gtgtgaactc    480
tataacattt tggccaaatg ccacagccga tctgcatatt ccaatggaca taatgcaaca    540
acaattgatg tcacattctc ttacacactt cgattggtcc gtacgtagta cttttttacat   600
aactgactca ggcgtttcct tcattgaaat gctcatctat tgccaagtac atagaatcca    660
cagtgcatag gtttatgaga tgcttggaag atgtacgatc gcctgcacta tattagtata    720
tttttttcagg cttacaaaa ccagaaagaa attaccgact gtaatactta atttccatga    780
ttttaatcgt atggtccgtg aggaaagagg aattttaggt aaaaaaaaac ctttgtctat    840
caaaacataa aagaaagaa aaaattaaa ttgaataagt cagcttttta gcatgaccac       900
agtaataata gtaatacgat atcagcatga gctgctaaac attaagaatt tttgaattgt    960
gttcgctgg                                                            969
```

<210> SEQ ID NO 4
<211> LENGTH: 1037
<212> TYPE: DNA
<213> ORGANISM: Saccharomyces cerevisiae

<400> SEQUENCE: 4

```
tttcggtagt gagatggcag ttcgaggggt tttttattca aaataataac ttctggcttt      60
tcgcttttat atagcagaaa aaaaagccgt cgaggcgcgc gcgttcatgc aatggctcag     120
taacctcggg atagaaaaag ggcaacaatg ttgagctatt ttaggcacag aaactttact     180
attcgaaaag ggcatccatt tcatttccga ttttctatct agctcactcg ataatcgtaa     240
tagtactttt ataaaacttt agtgcgggta ctgtgagagt gtgccgtaac tttggtttac     300
atttaaggtg cgaccagcaa tgtcactact tttacaacaa ccgccatatg gctcgagaat     360
ttcattatca catggaatgc ctgtgacaaa actgtgtaaa tatctaatag aaattagatg     420
tagctgtcac aaatatttac acaggaaaga gcctgtccta cgagtatctt acatgaagat     480
tcatagaacc aatttacttg cgaatgtgaa caacctttca acatcatttc aataccattt     540
tccctcctta tgtttggtgt cactgtaaag cggatcaaag caaaacatag aggtacggtg     600
gtgctaagat catgcatgac ctctgggtaa ttactacttc tcccgcttgt tttgagattc     660
tgtatataaa tatttcaaac aaaaggatag agcgcggatg gcaggcctta tagtaaaagt     720
tattcgtttt aatcatgtgt cagtatgaga ttctatgaca atagtatgag aagatagggt     780
gaagtaaaag tatctgtatg actatagagt gcagttatat tacaatatat tgaatagatc     840
ataatggtat gacgatatta aggaacattt aagttaatga cgtcatggtg gtatagatac     900
gcaattgagt gtgtttatgt attattgttg aaaagtagaa tatttttatg tttaggtgat     960
tttgatgata tttttatgta atattgacat aagtgcatat aaattgagtg gttagtatat    1020
ggtgcaaaag tggtaca                                                   1037
```

<210> SEQ ID NO 5
<211> LENGTH: 950
<212> TYPE: DNA
<213> ORGANISM: Saccharomyces cerevisiae

<400> SEQUENCE: 5

```
ttagtttgga acagcagtgt agataccgtc cttggataga gcgctggaga tagctggtct      60
caatctggtg gagtaccatg ggacaccagt gatgactcta gtgacttgat cagcgggaat     120
accagtcaac atagtggtga atcaccgta gttgaaaaca gcttcagcaa tttcaactgg      180
gtaagtttca gttggatgag cagcttggaa catatagtat tcagccaaat gagctctgat     240
atctgagacg tagacaccta attcgaccag gttaactctt tcgtcagagg gagataaagt     300
agtggtggct ggggcagcag cgacaccagc agcaatagca gcgacaccag caacaattga     360
agttagtttg accatttttt tcgattgaac ttttgtagat cttttttagtg aagatgtgag     420
ctcactcgaa tgtaaataac aatgccaaat tgtcggaaag agttaatcaa agctgctcta     480
tttatatgcc gttttttaat aagcgacgga cgaacagata aattgttgaa tagctatttc     540
actgctgata tttctcttac ttgggctccc ctatcccata ctcttcacca ctacaaatat     600
gcagttgccc tttcttcaac aatgcttttt ttatagatct cgtatacgga tccgcgcctt     660
tgtactacct atatcttatt atgatatata caggagcaca ggaatgttcg gtacagggat     720
gatacctta aaggaagttt tggcatgcct tgacaacttc aattaatctt tggccaagaa     780
aatgaaccag aaatcaaatt ttattctgtg ccctctgaac gagggcaata tccaatgttt     840
```

```
gacactaaac ggttgtcagg agaaaaattg aatgtttccc aaatcagaaa cattaaaatc    900
cctctatatg atcagaggag tcgtacctgt tagggtatga gcgaggaaac               950

<210> SEQ ID NO 6
<211> LENGTH: 982
<212> TYPE: DNA
<213> ORGANISM: Saccharomyces cerevisiae

<400> SEQUENCE: 6
aatgagttac cgtctgttac ttttgggacg gtttttgcac taagaacaga cgagtttacg    60
gttatcctca acaagcaagc aagtatttgc taatctagat gccattccga atcattactc   120
atacgttact attgagagat gttttacaat agatgagaag aatacaatgt ccagagctcc   180
tggtatgcta gagtgcatat tccaggtctt attcgaatca tcataccg tccatttcaa     240 caatggtgaa atgtggtcca catatatcag aaatcttaac atttagtgag gagagccagt   300
agaaaaatgt gcgcaagcgg aaagaagtca ttcacagaca cgtttaacaa acaccacca    360 cagcagcttt gtctcttgat tctgatcagt ttgccatcga agaagcaaaa ttgtggtgtt   420 attttttca aacaaaactt ttttggcaac agcagttttc ttctggatat ttgtacttta    480
tcatccaacc gatgaaagct ggtttcctgt caacctacat ttaaatggcc cgtacttctt   540
caaaaccgct agataagcaa attaacccaa cttttgagcg tcctaaattc cccttggctc   600
agaagactcg ttaatatggg aagtttaagt cctaccatat aatcaaattg gaagctttct   660
gtgttcgaat ggctattcta accgctgggc tattaatcag aggggaagtg aaatgaccga   720
gacgtattat acgtcatgtt gacatcaaca atttaaggaa aaaataaaa aaaagcaatg    780 aaaaagggtt tttttaagtt gaagacccct tcaaatata tgttgctttg aattgtatct    840
accgtctcgt ttcttctgct ttaccgtttt tttttgcctt ctttagatat gtcttttatg   900
cttgaaaggt ccggctttaa tgcattcatc taaacgtagt attcctattt ttgaactgct   960
accaatccac catgactttta ct                                           982

<210> SEQ ID NO 7
<211> LENGTH: 1010
<212> TYPE: DNA
<213> ORGANISM: Saccharomyces cerevisiae

<400> SEQUENCE: 7
tcctagagta gcgattcccc ttcgcgtatt cttacatctt cgaagagaac ttctggtgta    60
agtataataa atattatagc tctatcgaat ggtgcaatta tttaccaaat tctcaatagg   120
aatccataat actacatacg atactaatat tctagtattt ttatacttat tatttctttt   180
ttattacacc agcaatcgtt gcaaattatc ttctgataga atttctgagg gtatcctaaa   240
cttatgccat tttcttggac tgtaaatcat acttggatgt tgtgcattag tcaataatcg   300
gttcttgttc aacgattac atgtaaatga agggagaaat aattatggta atcatgcgg    360 cggtcctttt ggtgatgcag tatccatagt cactacataa caatcttagt caccttgtat   420
tgattcacca cataatcctg cagagcccgc tatgtcctta atctgcgcga taactctcct   480
acccctgaat tttgagagcg ccatagcaaa ccgataaagc tggcacaatt aaaggtatcg   540
gtgttgtcag aattaggtgc ctcctgcttt tttttttttc ctgctcttat atccgttata   600
tccgaatgat ttttatcgct tgtttaaaaa atactttccc gatatatata tatagtctcc   660
ctttaaattt gttccggta agttttaac accaataaat gaaaagaaat gactacggtg     720
atgaatatga gccgcgcatt gaatcaggtt atgtaagtat cagaacccct aattatgatg   780
```

| | | |
|---|---|---|
| tcactcttac ccttcgatgg ctaagcggcg actgggatgc cgggaaaagc tctacaaatc | 840 | |
| tactaaaaaa gtcaaatata cagctgtaaa cttctttcct cgtctacatc atggtaacga | 900 | |
| ttgttcaatc tttacttcgt gtctttttt tttctatgt actttctatt ccaacctatg | 960 | |
| tgaagactaa aattcacctt agtaaacgta aagacaatga cgataggtgc | 1010 | |

<210> SEQ ID NO 8
<211> LENGTH: 951
<212> TYPE: DNA
<213> ORGANISM: Saccharomyces cerevisiae

<400> SEQUENCE: 8

| | |
|---|---|
| tagttggagg ttggtgagta ccagattgct tacaaaagaa tagcgagcca acatttgctc | 60 |
| tgcctcaggc ctcttggtgc tgcttgaaga ctcatcttat atggcttttg tatgtcatga | 120 |
| tttgttcttg tacattatgt gttgatatta acaaattga ttttttttt tttgcgatag | 180 |
| caagcagata atgaaagaga caaggacttg aacatccga taagactgcg ccgatatcga | 240 |
| tcttacagtc cttcccttgt gtcatgactt tcggaaaagc atcctcgtcg actggtagtt | 300 |
| tgctgtctgt cacgtgctga agggtctgat acattttttt aaagataaga gacggggttt | 360 |
| acccttcgga ggactaagcg agatctccaa gtaaagatct cgcttatcaa gaaagcagcc | 420 |
| aagtgtggaa cgtccttttt tttggtttca aaaagatatt caacagttta cactgcagct | 480 |
| ttaattgcct caaaaggata tcatgaggtg atctagggtc agaagggaaa gattacagca | 540 |
| tcttgagttg aatcacatct gcaaaaggtg gtattattga cgttgctctt ccttaatgga | 600 |
| aactcatggg gtttggaaag gaggtgcggt aatctatttt tttcgaacac aaaacctaac | 660 |
| cttgaaaaga aactgtccaa tttcattgaa cttacctcag aacgggccgg agtctttgct | 720 |
| ttcagtctaa catggtctaa tttcttcgaa aagcttcatt taattgttag actgtggttt | 780 |
| tacaaggaaa aaaccagtgc tatactgaag cgatacccag aactaattac cttgtgtgac | 840 |
| gattcggctc agcgaaacgg acatggtaaa attgggaatt tgaaagcagg cagcagcctt | 900 |
| gtacagcgac atgacgatag gtttagaatc cccatcacgt acgagttgaa g | 951 |

<210> SEQ ID NO 9
<211> LENGTH: 952
<212> TYPE: DNA
<213> ORGANISM: Saccharomyces cerevisiae

<400> SEQUENCE: 9

| | |
|---|---|
| ccattcatat catttagtgc ttatggctac ttttcattcc tcaattattg taaattgacc | 60 |
| atcttaatta tatttctgat attgagtagg tggacttcat tagtattttt acaaatatta | 120 |
| tcaccttctt atgtaggatt agcattacat accctctaat taaaaaagt taacattaat | 180 |
| tacatttaa aaaaaattgt aatagtatga tagtaggacc tgacagccat ttgaataagg | 240 |
| tttcgagtgc tttaacgttc cactgatttt atgtagttca tatgggggtt agtctggttt | 300 |
| gaggaggaga atttcaggga agcagtggcc gttgaatctc cctgtagggc gctgattatt | 360 |
| tttatcctaa taatccaaaa atgacaatgt caataaagaa aacttaccga gttctgtgaa | 420 |
| tttctcccta aaaattact aattatacct gggcgagttt tgaactcttt ggcaaataaa | 480 |
| cttggggtaa acctttcgat tataaagacg ttactgctca aaaatgtgta gaagcataag | 540 |
| gagatattct ctcgtatgtt taattggagt tggctttttt ggactctgaa gtttgagtat | 600 |
| gggaggggaa gtaatcgaga ttagattccc tgatgttcac atatggggat aaagaatgct | 660 |
| ttttgggata tgattgtttc tttccgtcgt tacggttgta ggtgcaacga attgcgtaag | 720 |

-continued

```
ggtggctagc cgagatttaa tgacgacgca aagggaata actgtgacag gaagatgaat      780
tcacaaagtt tataaaaaga aagggcgatg cactgctaca tggttgaaca aggcactaca      840
taattcacag cttgtagctt gtaaataaaa agagcattca cgcgatatac gattttcaat      900
gatcactcta agaggaacgg cgaaaaatag aattcaatat gaactggaat gg             952
```

<210> SEQ ID NO 10
<211> LENGTH: 967
<212> TYPE: DNA
<213> ORGANISM: Saccharomyces cerevisiae

<400> SEQUENCE: 10

```
gatttaatac agtacctttc ttcgctagga tctatatgcg aatatatcac atatgtaaat       60
tataagctca tcgcaaaacc aaaaaaaaaa aaatttcaa taattttca ctaatcttca       120 aaaacaaatg gggtaacccg tacaagagtt attaaaaccc aaaatgacaa atcgcgaca      180 attcaatcct acttaattag caataacata ctagcggtag agctactatc acatgttgaa      240
ccttgaatgc tcaattcatt gtactcaata ctgctatcaa agaaaaaaa atgtattaat       300 tatattcttg tcaaaatcaa ttttacacta aagaggaaa atgttcttca gtcctagtaa      360
cattagtttt ctcccttttgc tagagacttt acataatatc ctagaaggta aaattcgata      420
atacagcagt aaagtcgtat attggtagca atccttggtg acgctgactt ttttttttg      480 taatttatt gtttagttca tgataaaaa cttcaaatca cttttaatct ggtagacaga      540
gaaaacaaat cgaaacgaaa atagagaact acgaataaaa aatataagt ggagaagatc      600 gtcactacgc attaaacaat attgatcgct caatgccagt actgcgcgta aaagtttagt      660
aacttaacga tttaggcaca atttgagaaa aatttcgccc tgcagtaagt atgttattca      720
gtacgatata aagctgaggt tttatgctgg caacgttcag atttttttagg ttatcagcaa      780 tgttaaaata ttaaatagga tacttttatt gtttgagacc accctcaatg ccagatatgt      840
taaacgcttt tttctggagt gaggtatcat agaaaaaggc tcgagtacat caagcactta      900
aaggttcaac actctactgt tacttcttta agctaagcta ttcatacata atagtccatc      960
aaagtgg                                                                967
```

<210> SEQ ID NO 11
<211> LENGTH: 795
<212> TYPE: DNA
<213> ORGANISM: Saccharomyces cerevisiae

<400> SEQUENCE: 11

```
aatgtcgata ctgtgttacg tttgcaagga aaagatttag ttgcgattag ccattcattc       60
ttgtggaaac ttctttaaaa agggatggcg atggagtact tatgtccaat tatgaagtca      120
aatttatttt caaaccgtta cacgtagatt attttcctgc agtggtaagt atctttgaag      180
tgttgaaagt tttttggcac atattttttt gcggatgtgg gcctgagttt cctgttagaa      240
acaaagatat gcttaaaact aaataacatt ggaaattagg gcatagtctt caatgtttata      300 cttaaacatc acagcaggag attgagatga ttgaaagaat ggtgcaagaa atgattcatt      360
aacattcttc caagttttgc aatatttgca agtattacta tcagacttta gttgaagtga      420
ctatgctatt accaaatttc actggagcca gaaaaataaa gatcacttag agacaaagaa      480
aagtaacatc ttcaacataa gccggagctc aaagtagga atcggataa gaaacttgat      540 tctgttattt caagtgattt tttgctgtat cgcccacgtt cttgttgtag atgttttgta      600
gatgtgggac cgaaagtaag tgaacagtga agtaaacaga ataggattct aaaaaagagc      660
```

-continued

```
ttataaactg ttctttaaaa ttttttcttt cgtgaatgtc ctcgagctat ctcaaagaaa       720
acgaaatctt cattcaactt aagtgtaggt attatttgct gtttcatcaa atgcggcacc       780
aaagtggaag tattc                                                       795

<210> SEQ ID NO 12
<211> LENGTH: 762
<212> TYPE: DNA
<213> ORGANISM: Saccharomyces cerevisiae

<400> SEQUENCE: 12 tttcttttc cctatttctc actggttgac agaaatcagt gtgctatcat cctaccatat        60
gcgctaaact tattgtcttt ctcctcctag agatgctgta ttccatgcat attctgaacg      120
atgggttggt gttttatca agcaaggtta atcacatggc gtggcttgct ccacacatca       180
gtagaaaacg cataccgcag cggaatcctt aataataag tgatttttact gttcatcaac      240 tacaatcgga ctcttccaca attacccttc ttgttttcca catttactgt taaatgaagg      300
gatgtacaga aggcttagga aaacctgtgc tgaatactgg atggacactg cattcccaca      360
gtgaaacttt tatagataca ctgtcagtta ttttcgaact ttcatcaagt tgctgagttt      420
tagtatccct ttgccttagc tatatgtttg aatgagcaaa atatttgcaa tgtctctagc      480
tttcttgaaa tattggttta tattgagggc ttggtaagat ttcaaatttc actttgaaat      540
actcaggaga aaaatcatgc tcttttgata atttggtgac taaacataca taaaacagtt      600
taattttggg tggtaatggc tgtgtgacta gctatagaaa gaaaaaaatt aaaaaaaaaa      660
aaaaaaatca agtagttcct gcactgcgac gtccattata gcattatgaa ttggtccctg      720
atttacgcat gcgataaact attttttagcg cagccgcata tt                       762

<210> SEQ ID NO 13
<211> LENGTH: 726
<212> TYPE: DNA
<213> ORGANISM: Saccharomyces cerevisiae

<400> SEQUENCE: 13
actgtatata aagaggact gcaatagcac aagattaaga tagaatggct tcaaacagcc        60
gccttttata catattggta aaagctcgcg aatcgcacca tatcccttat cctgtaatca      120
aatcgatcta ggtgcagata cagatcaatt cataaaaaga aattgaagca ccagtttatc      180
actactacac tatctttttc tttttttttt tttttgcga gtttcgccc tttgttcaat        240 atcacttgat aagttgtggg ctttttctgt cactcattcg gcttaaaaag tattcgttct      300 tttgtgttt atgaaaaggg aacgtgatat aaaaaaacat cctttggtgt gggacatggg      360 ctttttgttta gagaatggtt atcactaccg ccccccaccct tgaaagccac agaaaatgaa     420
aaagtatgtg aataaggtgt gaactctata acattttggc caaatgccac agccgatctg     480
catattccaa tggacataat gcaacaacaa ttgatgtcac attctcttac acacttcgat     540
tggtccgtac gtagtacttt ttacataact gactcaggcg tttccttcat tgaaatgctc     600
atctattgcc aagtacatag aatccacagt gcataggttt atgagatgct tggaagatgt     660
acgatcgcct gcactatatt agtatatttt ttcaggcttt acaaaaccag aagaaatta     720 ccgact                                                                726

<210> SEQ ID NO 14
<211> LENGTH: 849
<212> TYPE: DNA
<213> ORGANISM: Saccharomyces cerevisiae
```

<400> SEQUENCE: 14

```
ataataactt ctggcttttc gcttttatat agcagaaaaa aaagccgtcg aggcgcgcgc      60
gttcatgcaa tggctcagta acctcgggat agaaaaaggg caacaatgtt gagctatttt     120
aggcacagaa actttactat tcgaaaaggg catccatttc atttccgatt ttctatctag     180
ctcactcgat aatcgtaata gtacttttat aaaactttag tgcgggtact gtgagagtgt     240
gccgtaactt tggtttacat ttaaggtgcg accagcaatg tcactacttt tacaacaacc     300
gccatatggc tcgagaattt cattatcaca tggaatgcct gtgacaaaac tgtgtaaata     360
tctaatagaa attagatgta gctgtcacaa atatttacac aggaaagagc ctgtcctacg     420
agtatcttac atgaagattc atagaaccaa tttacttgcg aatgtgaaca acctttcaac     480
atcatttcaa taccattttc cctccttatg tttggtgtca ctgtaaagcg atcaaagca      540
aaacatagag gtacggtggt gctaagatca tgcatgacct ctgggtaatt actacttctc     600
ccgcttgttt tgagattctg tatataaata tttcaaacaa aaggatagag cgcggatggc     660
aggccttata gtaaaagtta ttcgtttta tcatgtgtca gtatgagatt ctatgacaat     720
agtatgagaa datagggtga agtaaaagta tctgtatgac tatagagtgc agttatatta     780
caatatattg aatagatcat aatggtatga cgatattaag gaacatttaa gttaatgacg     840
tcatggtgg                                                             849
```

<210> SEQ ID NO 15
<211> LENGTH: 712
<212> TYPE: DNA
<213> ORGANISM: Saccharomyces cerevisiae

<400> SEQUENCE: 15

```
agataccgtc cttggataga gcgctggaga tagctggtct caatctggtg gagtaccatg      60
ggacaccagt gatgactcta gtgacttgat cagcgggaat accagtcaac atagtggtga     120
aatcaccgta gttgaaaaca gcttcagcaa tttcaactgg gtaagtttca gttggatgag     180
cagcttggaa catatagtat tcagccaaat gagctctgat atctgagacg tagacaccta     240
attcgaccag gttaactctt tcgtcagagg gagataaagt agtggtggct ggggcagcag     300
cgacaccagc agcaatagca gcgacaccag caacaattga agttagtttg accattttt      360
tcgattgaac ttttgtagat cttttagtg aagatgtgag ctcactcgaa tgtaaataac     420
aatgccaaat tgtcggaaag agttaatcaa agctgtctca tttatatgcc gttttttaat     480
aagcgacgga cgaacagata aattgttgaa tagctatttc actgctgata tttctcttac     540
ttgggctccc ctatcccata ctcttcacca ctacaaatat gcagttgccc tttcttcaac     600
aatgcttttt ttatagatct cgtatacgga tccgcgcctt tgtactacct atatcttatt     660
atgatatata caggagcaca ggaatgttcg gtacagggat gatacctta aa              712
```

<210> SEQ ID NO 16
<211> LENGTH: 893
<212> TYPE: DNA
<213> ORGANISM: Saccharomyces cerevisiae

<400> SEQUENCE: 16

```
ttgggacggt ttttgcacta agaacagacg agtttacggt tatcctcaac aagcaagcaa      60
gtatttgcta atctagatgc cattccgaat cattactcat acgttactat tgagagatgt     120
tttacaatag atgagaagaa tacaatgtcc agagctcctg gtatgctaga gtgcatattc     180
caggtcttat tcgaatcata tcataccgtc catttcaaca atggtgaaat gtggtccaca     240
```

-continued

```
tatatcagaa atcttaacat ttagtgagga gagccagtag aaaaatgtgc gcaagcggaa      300
agaagtcatt cacagacacg tttaacaaaa caccaccaca gcagctttgt ctcttgattc      360
tgatcagttt gccatcgaag aagcaaaatt gtggtgttat ttttttcaaa caaaactttt      420
ttggcaacag cagttttctt ctggatattt gtactttatc atccaaccga tgaaagctgg     480
tttcctgtca acctacattt aaatggcccg tacttcttca aaaccgctag ataagcaaat     540
taacccaact tttgagcgtc ctaaattccc cttggctcag aagactcgtt aatatgggaa     600
gtttaagtcc taccatataa tcaaattgga agctttctgt gttcgaatgg ctattctaac     660
cgctgggcta ttaatcagag gggaagtgaa atgaccgaga cgtattatac gtcatgttga     720
catcaacaat ttaaggaaaa aaataaaaaa aagcaatgaa aagggttttt tttaagttga     780
agaccctttt caaatatatg ttgctttgaa ttgtatctac cgtctcgttt cttctgcttt     840 accgttttt tttgccttct ttagatatgt ctttttatgct tgaaaggtcc ggc            893

<210> SEQ ID NO 17
<211> LENGTH: 757
<212> TYPE: DNA
<213> ORGANISM: Saccharomyces cerevisiae

<400> SEQUENCE: 17
ttcgcgtatt cttacatctt cgaagagaac ttctggtgta agtataataa atattatagc      60
tctatcgaat ggtgcaatta tttaccaaat tctcaatagg aatccataat actacatacg     120
atactaatat tctagtattt ttatacttat tatttctttt ttattacacc agcaatcgtt     180
gcaaattatc ttctgataga atttctgagg gtatcctaaa cttatgccat tttcttggac     240
tgtaaatcat acttggatgt tgtgcattag tcaataatcg gttcttgttc caacgattac     300
atgtaaatga agggagaaat aattatggta aatcatgcgg cggtcctttt ggtgatgcag     360
tatccatagt cactacataa caatcttagt caccttgtat tgattcacca cataatcctg     420
cagagcccgc tatgtcctta atctgcgcga taactctcct accccctgaat tttgagagcg     480 ccatagcaaa ccgataaagc tggcacaatt aaaggtatcg gtgttgtcag aattaggtgc     540
ctcctgcttt ttttttttc ctgctcttat atccgttata tccgaatgat ttttatcgct     600
tgtttaaaaa atactttccc gatatatata tatagtctcc ctttaaattt gtttccggta     660
agtttttaac accaataaat gaaaagaaat gactacggtg atgaatatga gccgcgcatt     720
gaatcaggtt atgtaagtat cagaaccccct aattatg                             757

<210> SEQ ID NO 18
<211> LENGTH: 714
<212> TYPE: DNA
<213> ORGANISM: Saccharomyces cerevisiae

<400> SEQUENCE: 18
ccagattgct tacaaaagaa tagcgagcca acatttgctc tgcctcaggc ctcttggtgc      60
tgcttgaaga ctcatcttat atggcttttg tatgtcatga tttgttcttg tacattatgt     120
gttgatatta aacaaattga ttttttttttt tttgcgatag caagcagata atgaaagaga     180
caaggacttg gaacatccga taagactgcg ccgatatcga tcttacagtc cttcccttgt     240
gtcatgactt tcgaaaagc atcctcgtcg actggtagtt tgctgtctgt cacgtgctga     300
agggtctgat acatttttttt aaagataaga gacgggggttt acccttcgga ggactaagcg     360
agatctccaa gtaagatctc cgcttatcaa gaaagcagcc aagtgtggaa cgtccttttt     420
tttggtttca aaaagatatt caacagttta cactgcagct ttaattgcct caaaaggata     480
```

```
tcatgaggtg atctagggtc agaagggaaa gattacagca tcttgagttg aatcacatct    540
gcaaaaggtg gtattattga cgttgctctt ccttaatgga aactcatggg gtttggaaag    600
gaggtgcggt aatctatttt tttcgaacac aaaacctaac cttgaaaaga aactgtccaa    660
tttcattgaa cttacctcag aacgggccgg agtctttgct ttcagtctaa catg          714
```

<210> SEQ ID NO 19
<211> LENGTH: 721
<212> TYPE: DNA
<213> ORGANISM: Saccharomyces cerevisiae

<400> SEQUENCE: 19

```
ttatggctac ttttcattcc tcaattattg taaattgacc atcttaatta tatttctgat     60
attgagtagg tggacttcat tagtattttt acaaatatta tcaccttctt atgtaggatt    120
agcattacat accctctaat taaaaaaagt taacattaat tacattttaa aaaaaattgt    180
aatagtatga tagtaggacc tgacagccat ttgaataagg tttcgagtgc tttaacgttc    240
cactgatttt atgtagttca tatgggggtt agtctggttt gaggaggaga atttcaggga    300
agcagtggcc gttgaatctc cctgtagggc gctgattatt tttatcctaa taatccaaaa    360
atgacaatgt caataaagaa aacttaccga gttctgtgaa tttctcccta aaaaattact    420
aattataccc gggcgagttt tgaactcttt ggcaaataaa cttggggtaa acctttcgat    480
tataaagacg ttactgctca aaaatgtgta gaagcataag gagatattct ctcgtatgtt    540
taattggagt tggcttttttt ggactctgaa gtttgagtat gggagggggaa gtaatcgaga    600 ttagattccc tgatgttcac atatggggat aaagaatgct ttttgggata tgattgtttc    660
tttccgtcgt tacggttgta ggtgcaacga attgcgtaag ggtggctagc cgagatttaa    720
t                                                                    721
```

<210> SEQ ID NO 20
<211> LENGTH: 725
<212> TYPE: DNA
<213> ORGANISM: Saccharomyces cerevisiae

<400> SEQUENCE: 20

```
gctaggatct atatgcgaat atatcacata tgtaaattat aagctcatcg caaaaccaaa     60
aaaaaaaaaa ttttcaataa tttttcacta atcttcaaaa acaaatgggg taacccgtac    120
aagagttatt aaaacccaaa atgacaaaat cgcgacaatt caatcctact taattagcaa    180
taacatacta gcggtagagc tactatcaca tgttgaacct tgaatgctca attcattgta    240
ctcaatactg ctatcaaaag aaaaaaaatg tattaattat attcttgtca aaatcaattt    300
tacactataa gaggaaaatg ttcttcagtc ctagtaacat tagttttctc cctttgctag    360
agactttaca taatatccta gaaggtaaaa ttcgataata cagcagtaaa gtcgtatatt    420
ggtagcaatc cttggtgacg ctgactttt tttttgtaa ttttattgtt tagttcatga    480
taaaaaactt caaatcactt ttaatctggt agacagagaa aacaaatcga acgaaaata    540 gagaactacg aataaaaaaa tataagtgga gaagatcgtc actacgcatt aaacaatatt    600
gatcgctcaa tgccagtact gcgcgtaaaa gtttagtaac ttaacgattt aggcacaatt    660
tgagaaaaat ttcgccctgc agtaagtatg ttattcagta cgatataaag ctgaggtttt    720
atgct                                                                725
```

```
<210> SEQ ID NO 21
<211> LENGTH: 20
<212> TYPE: DNA
<213> ORGANISM: Saccharomyces cerevisiae

<400> SEQUENCE: 21
ttcgttggat tgagtaagaa                                           20

<210> SEQ ID NO 22
<211> LENGTH: 20
<212> TYPE: DNA
<213> ORGANISM: Saccharomyces cerevisiae

<400> SEQUENCE: 22
gcgaataacc aaaacgagac                                           20

<210> SEQ ID NO 23
<211> LENGTH: 22
<212> TYPE: DNA
<213> ORGANISM: Saccharomyces cerevisiae

<400> SEQUENCE: 23 tgttttgct atattacgtg gg                                         22

<210> SEQ ID NO 24
<211> LENGTH: 20
<212> TYPE: DNA
<213> ORGANISM: Saccharomyces cerevisiae

<400> SEQUENCE: 24
tttcggtagt gagatggcag                                           20

<210> SEQ ID NO 25
<211> LENGTH: 20
<212> TYPE: DNA
<213> ORGANISM: Saccharomyces cerevisiae

<400> SEQUENCE: 25
ttagtttgga acagcagtgt                                           20

<210> SEQ ID NO 26
<211> LENGTH: 20
<212> TYPE: DNA
<213> ORGANISM: Saccharomyces cerevisiae

<400> SEQUENCE: 26
aatgagttac cgtctgttac                                           20

<210> SEQ ID NO 27
<211> LENGTH: 20
<212> TYPE: DNA
<213> ORGANISM: Saccharomyces cerevisiae

<400> SEQUENCE: 27
tcctagagta gcgattcccc                                           20

<210> SEQ ID NO 28
<211> LENGTH: 20
<212> TYPE: DNA
<213> ORGANISM: Saccharomyces cerevisiae

<400> SEQUENCE: 28
tagttggagg ttggtgagta                                           20
```

<210> SEQ ID NO 29
<211> LENGTH: 20
<212> TYPE: DNA
<213> ORGANISM: Saccharomyces cerevisiae

<400> SEQUENCE: 29
ccattcatat catttagtgc                    20

<210> SEQ ID NO 30
<211> LENGTH: 25
<212> TYPE: DNA
<213> ORGANISM: Saccharomyces cerevisiae

<400> SEQUENCE: 30
gatttaatac agtacctttc ttcgc              25

<210> SEQ ID NO 31
<211> LENGTH: 20
<212> TYPE: DNA
<213> ORGANISM: Saccharomyces cerevisiae

<400> SEQUENCE: 31
gcacttctag taagcacatg                    20

<210> SEQ ID NO 32
<211> LENGTH: 20
<212> TYPE: DNA
<213> ORGANISM: Saccharomyces cerevisiae

<400> SEQUENCE: 32
gcactaaact aaaaccgtga                    20

<210> SEQ ID NO 33
<211> LENGTH: 20
<212> TYPE: DNA
<213> ORGANISM: Saccharomyces cerevisiae

<400> SEQUENCE: 33
ccagcgaaca caattcaaaa                    20

<210> SEQ ID NO 34
<211> LENGTH: 20
<212> TYPE: DNA
<213> ORGANISM: Saccharomyces cerevisiae

<400> SEQUENCE: 34
tgtaccactt ttgcaccata                    20

<210> SEQ ID NO 35
<211> LENGTH: 20
<212> TYPE: DNA
<213> ORGANISM: Saccharomyces cerevisiae

<400> SEQUENCE: 35
gtttcctcgc tcatacccta                    20

<210> SEQ ID NO 36
<211> LENGTH: 20
<212> TYPE: DNA
<213> ORGANISM: Saccharomyces cerevisiae

```
<400> SEQUENCE: 36
agtaaagtca tggtggattg                                              20

<210> SEQ ID NO 37
<211> LENGTH: 20
<212> TYPE: DNA
<213> ORGANISM: Saccharomyces cerevisiae

<400> SEQUENCE: 37
gcacctatcg tcattgtctt                                              20

<210> SEQ ID NO 38
<211> LENGTH: 20
<212> TYPE: DNA
<213> ORGANISM: Saccharomyces cerevisiae

<400> SEQUENCE: 38
cttcaactcg tacgtgatgg                                              20

<210> SEQ ID NO 39
<211> LENGTH: 20
<212> TYPE: DNA
<213> ORGANISM: Saccharomyces cerevisiae

<400> SEQUENCE: 39
ccattccagt tcatattgaa                                              20

<210> SEQ ID NO 40
<211> LENGTH: 25
<212> TYPE: DNA
<213> ORGANISM: Saccharomyces cerevisiae

<400> SEQUENCE: 40
ccactttgat ggactattat gtatg                                        25

<210> SEQ ID NO 41
<211> LENGTH: 62
<212> TYPE: DNA
<213> ORGANISM: Saccharomyces cerevisiae

<400> SEQUENCE: 41
gcattagcgg ccgcgaaatt aatacgactc actataggga gaaatgtcga tactgtgtta   60
cg                                                                 62

<210> SEQ ID NO 42
<211> LENGTH: 67
<212> TYPE: DNA
<213> ORGANISM: Saccharomyces cerevisiae

<400> SEQUENCE: 42
gcattagcgg ccgcgaaatt aatacgactc actataggga gatttctttt tccctatttc   60
tcactgg                                                            67

<210> SEQ ID NO 43
<211> LENGTH: 64
<212> TYPE: DNA
<213> ORGANISM: Saccharomyces cerevisiae

<400> SEQUENCE: 43
gcattagcgg ccgcgaaatt aatacgactc actataggga gaactgtata taaagagga    60 ctgc                                                               64
```

-continued

<210> SEQ ID NO 44
<211> LENGTH: 64
<212> TYPE: DNA
<213> ORGANISM: Saccharomyces cerevisiae

<400> SEQUENCE: 44
gcattagcgg ccgcgaaatt aatacgactc actataggga gaataataac ttctggcttt    60
tcgc                                                                 64

<210> SEQ ID NO 45
<211> LENGTH: 62
<212> TYPE: DNA
<213> ORGANISM: Saccharomyces cerevisiae

<400> SEQUENCE: 45
gcattagcgg ccgcgaaatt aatacgactc actataggga gaagataccg tccttggata    60
ga                                                                   62

<210> SEQ ID NO 46
<211> LENGTH: 66
<212> TYPE: DNA
<213> ORGANISM: Saccharomyces cerevisiae

<400> SEQUENCE: 46
gcattagcgg ccgcgaaatt aatacgactc actataggga gattgggacg gttttgcac     60 taagaa                                                               66

<210> SEQ ID NO 47
<211> LENGTH: 62
<212> TYPE: DNA
<213> ORGANISM: Saccharomyces cerevisiae

<400> SEQUENCE: 47
gcattagcgg ccgcgaaatt aatacgactc actataggga gattcgcgta ttcttacatc    60
tt                                                                   62

<210> SEQ ID NO 48
<211> LENGTH: 62
<212> TYPE: DNA
<213> ORGANISM: Saccharomyces cerevisiae

<400> SEQUENCE: 48
gcattagcgg ccgcgaaatt aatacgactc actataggga gaccagattg cttacaaaag    60
aa                                                                   62

<210> SEQ ID NO 49
<211> LENGTH: 62
<212> TYPE: DNA
<213> ORGANISM: Saccharomyces cerevisiae

<400> SEQUENCE: 49
gcattagcgg ccgcgaaatt aatacgactc actataggga gattatggct acttttcatt    60
cc                                                                   62

<210> SEQ ID NO 50
<211> LENGTH: 62
<212> TYPE: DNA
<213> ORGANISM: Saccharomyces cerevisiae -continued

```
<400> SEQUENCE: 50
gcattagcgg ccgcgaaatt aatacgactc actataggga gagctaggat ctatatgcga    60
at                                                                   62

<210> SEQ ID NO 51
<211> LENGTH: 41
<212> TYPE: DNA
<213> ORGANISM: Saccharomyces cerevisiae

<400> SEQUENCE: 51
tttttttttt tttttttttt tgaatacttc cactttggtg c                        41

<210> SEQ ID NO 52
<211> LENGTH: 41
<212> TYPE: DNA
<213> ORGANISM: Saccharomyces cerevisiae

<400> SEQUENCE: 52
tttttttttt tttttttttt taatatgcgg ctgcgctaaa a                        41

<210> SEQ ID NO 53
<211> LENGTH: 41
<212> TYPE: DNA
<213> ORGANISM: Saccharomyces cerevisiae

<400> SEQUENCE: 53
tttttttttt tttttttttt tagtcggtaa tttctttctg g                        41

<210> SEQ ID NO 54
<211> LENGTH: 46
<212> TYPE: DNA
<213> ORGANISM: Saccharomyces cerevisiae

<400> SEQUENCE: 54
tttttttttt tttttttttt tccaccatga cgtcattaac ttaaat                   46

<210> SEQ ID NO 55
<211> LENGTH: 41
<212> TYPE: DNA
<213> ORGANISM: Saccharomyces cerevisiae

<400> SEQUENCE: 55
tttttttttt tttttttttt ttttaaaggt atcatccctg t                        41

<210> SEQ ID NO 56
<211> LENGTH: 41
<212> TYPE: DNA
<213> ORGANISM: Saccharomyces cerevisiae

<400> SEQUENCE: 56
tttttttttt tttttttttt tgccggacct ttcaagcata a                        41

<210> SEQ ID NO 57
<211> LENGTH: 41
<212> TYPE: DNA
<213> ORGANISM: Saccharomyces cerevisiae

<400> SEQUENCE: 57
tttttttttt tttttttttt tcataattag gggttctgat a                        41
```

```
<210> SEQ ID NO 58
<211> LENGTH: 41
<212> TYPE: DNA
<213> ORGANISM: Saccharomyces cerevisiae

<400> SEQUENCE: 58
tttttttttt tttttttttt tcatgttaga ctgaaagcaa a                               41

<210> SEQ ID NO 59
<211> LENGTH: 41
<212> TYPE: DNA
<213> ORGANISM: Saccharomyces cerevisiae

<400> SEQUENCE: 59
tttttttttt tttttttttt tattaaatct cggctagcca c                               41

<210> SEQ ID NO 60
<211> LENGTH: 41
<212> TYPE: DNA
<213> ORGANISM: Saccharomyces cerevisiae

<400> SEQUENCE: 60
tttttttttt tttttttttt tagcataaaa cctcagcttt a                               41
```